United States Patent [19]

Yokoi et al.

[11] Patent Number: 5,020,539
[45] Date of Patent: Jun. 4, 1991

[54] ULTRASONIC ENDOSCOPE APPARATUS

[75] Inventors: Takeshi Yokoi; Yoshihito Horikawa, both of Hachioji, Japan

[73] Assignee: Olympus Optical Co., Ltd., Tokyo, Japan

[21] Appl. No.: 320,607

[22] Filed: Mar. 8, 1989

[30] Foreign Application Priority Data

Mar. 30, 1988 [JP] Japan .................. 63-74728
Apr. 22, 1988 [JP] Japan .............. 63-54203[U]
May 31, 1988 [JP] Japan .................. 63-131677

[51] Int. Cl.$^5$ .............................................. A61B 8/12
[52] U.S. Cl. ..................... 128/662.06; 128/4
[58] Field of Search ..................... 128/662.06, 4

[56] References Cited

U.S. PATENT DOCUMENTS

| | | | |
|---|---|---|---|
| 3,938,502 | 2/1976 | Bom | 128/662.06 |
| 4,327,738 | 5/1982 | Green et al. | 128/662.06 |
| 4,375,818 | 3/1983 | Suwaki et al. | 128/4 |
| 4,391,282 | 7/1983 | Ando et al. | 128/662.06 |
| 4,433,692 | 2/1984 | Baba | 128/662.06 |
| 4,489,728 | 12/1984 | Matsuo et al. | 128/662.06 |
| 4,494,549 | 1/1985 | Namba et al. | 128/662.06 |
| 4,572,201 | 2/1986 | Kondo et al. | 128/662.06 |
| 4,674,515 | 6/1987 | Andou et al. | 128/662.06 |
| 4,802,487 | 2/1989 | Martin et al. | 128/662.06 |

FOREIGN PATENT DOCUMENTS 3618906 12/1986 Fed. Rep. of Germany .
3619195 1/1987 Fed. Rep. of Germany .
3716963 11/1987 Fed. Rep. of Germany .
3716964 11/1987 Fed. Rep. of Germany .

OTHER PUBLICATIONS

Translation of an Office Action re: DE 3618906A1.

Primary Examiner—Francis Jaworski
Attorney, Agent, or Firm—Stevens, Davis, Miller & Mosher

[57] ABSTRACT

An ultrasonic endoscope apparatus having a distal end cap provided with an ultrasonic transmission window through which an ultrasonic beam is transmitted in a radial direction perpendicular to the axis of a probe of the apparatus, and a cylindrical member located adjacent to the ultrasonic transmission window. The cylindrical member extends in parallel with the axis of the distal end of the probe.

22 Claims, 19 Drawing Sheets

Range of Ultrasonic Laminagram Image

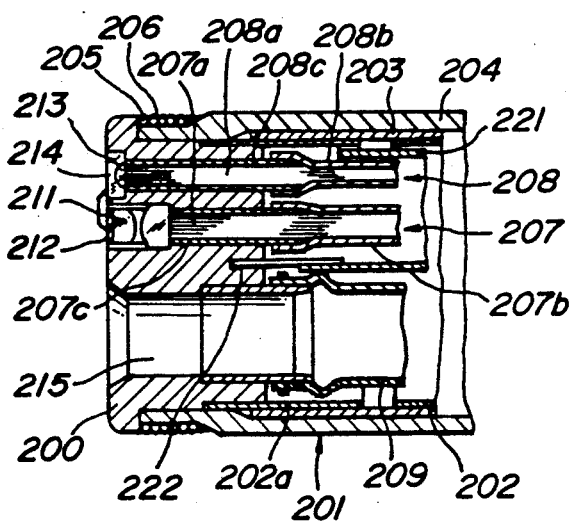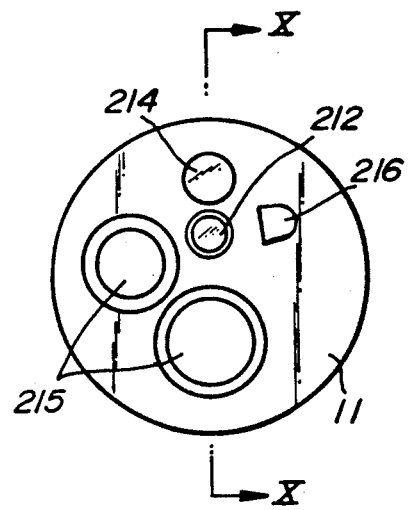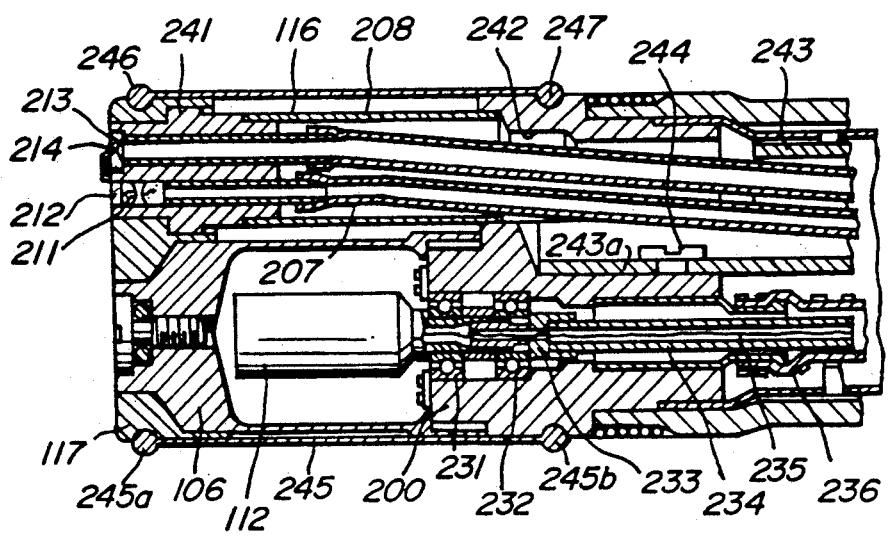

Rotational Locus

Range of Ultrasonic Laminagram Image

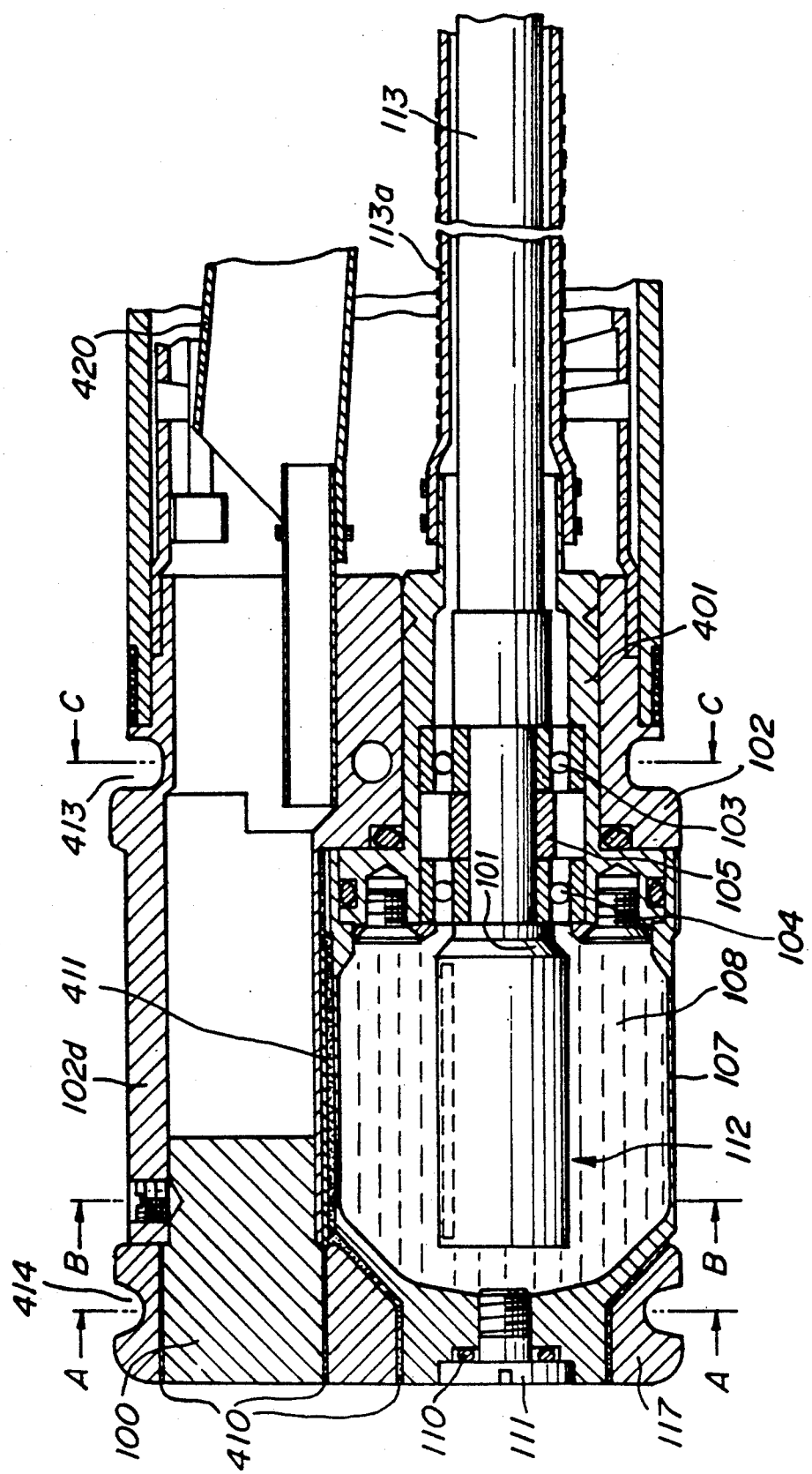

ULTRASONIC ENDOSCOPE APPARATUS

BACKGROUND OF THE INVENTION

1. Field of the Invention

The present invention relates to an ultrasonic endoscope apparatus for viewing a body cavity, more particularly to an improvement of the construction of a distal end of an insertion portion having an ultrasonic vibrating element and an observation window.

2. Description of the Related Art

Several kinds of ultrasonic endoscope apparatuses having a probe of which is inserted in a body cavity to carry out a precise ultrasonic diagnosis of the state of the cavity have been proposed. U.S. Pat. Nos. 3,817,089 and 4,674,515 and Japanese Unexamined Patent Publication Kokai Sho 61-168,337, for example, discloses an ultrasonic endoscope apparatus in which a rotatable rotor directs an ultrasonic beam emitted from an ultrasonic vibrating element to carry out the so-called radial scan in a plane perpendicular to the center axis of the probe, the circumference of the rotor being covered with a distal end cap having an ultrasonic transmission window, and a side view or an oblique forward view observation window being provided in a side face of a rear end portion of the distal end cap.

U.S. Pat. No. 4,327,738 discloses an ultrasonic endoscope apparatus in which an electronic linear scan type ultrasonic vibrating unit is provided in a distal end of a probe in parallel with the central axis of the probe, and an optical viewing system having an observation window at the front thereof is provided at the rear of the vibrating unit.

Nevertheless, although the former endoscope apparatus can obtain a laminagram image over a broad scope of, for example 360 degrees, when the probe is inserted in a body cavity, since the field of view in front of the optical observation window of the probe is not fully covered, the probe may damage a mucous membrane or a diseased portion of the body cavity if a narrow portion or a portion at which bleeding easily occurs, such as a varix, exists in the body cavity. Further, when the operator attempts to insert the probe into the depths of an internal organ having many bent tubes, such as the large intestine, it is not possible to determine the direction in which the probe should be inserted, and thus the insertion of the probe becomes difficult.

On the other hand, although a front view is easily obtained in the latter endoscope apparatus when the probe is inserted, if the length of the distal end portion of the probe is too long, the probe can not be easily inserted into bent internal organs, and thus the length of a hard end portion of the probe is limited. Therefore, the length of the ultrasonic vibrating un provided in the hard end portion of the probe is limited to 3 cm, and therefore, a problem arises in that an ultrasonic laminagram image having only a narrow breadth of 3 cm can be obtained. Further, only an ultrasonic laminagram image in parallel with the axis of the probe can be obtained, and therefore, in order to ensure that a diseased portion in an internal organ is fully observed, the distal end of the probe must be inserted in the organ while rotating the probe through 360 degrees, and thus a diagnosis requires much time and the patient is subjected to much pain.

SUMMARY OF THE INVENTION

The present invention is intended to solve the above problems, and the object of the present invention is to provide an ultrasonic endoscope apparatus for viewing a body cavity, by which an ultrasonic laminagram image can be obtained over a scope of approximately 360 degrees.

According to the present invention, there is provided an ultrasonic endoscope apparatus, for viewing a body cavity, which comprises a distal end support member, a distal end cap, an ultrasonic vibrating unit, and a cylindrical member.

The distal end cap is supported by a front end of the distal end support member and is provided with an ultrasonic transmission window for transmitting an ultrasonic beam in a radial direction perpendicular to the axis of the distal end support member. The ultrasonic transmission window extends substantially completely around the axis of the distal end support member. The ultrasonic vibrating unit is provided in the distal end cap, and emits and receives an ultrasonic beam through the ultrasonic transmission window. The cylindrical member is supported by the front end of the distal end support member and located adjacent to the ultrasonic transmission window. The cylindrical member extends in parallel with the axis of the distal end support member and encloses an optical viewing system having a visual field which faces at least frontward.

According to the present invention, only a small portion of an ultrasonic beam is incident on the cylindrical member provided in the distal end of the probe from which the ultrasonic beam is emitted, and thus the rate of deterioration of the ultrasonic image due to the cylindrical member is low. Further, the least possible number of members for obtaining a front view is provided in the cylindrical member, and therefore, since deterioration of the ultrasonic image is kept to the minimum, an ultrasonic laminagram image covering a wide range of, for example, more than 300 degrees, is obtained.

BRIEF DESCRIPTION OF THE DRAWINGS

The present invention may be more fully understood from the description of preferred embodiments of the invention set forth below, together with the accompanying drawings, in which:

FIG. 2c is a sectional view taken along the line IIC—IIC of FIG. 2a;

FIG. 2d is a sectional view taken along the line IID—IID of FIG. 2a;

FIG. 2e is a sectional view taken along the line IIE—IIE of FIG. 2a;

FIG. 8b is a side view of the fifth embodiment of FIG. 8a;

FIG. 10 is a sectional view taken along the line X—X of FIG. 11;

FIG. 11 is a front view of a distal end of a probe of the sixth embodiment of the present invention;

FIG. 12 is a sectional view taken along the line XII—XII of FIG. 13;

FIG. 16b is a front view of the distal end of FIG. 16a;

FIG. 16c is a sectional view of taken along the line XVIC—XVIC of FIG. 16a;

FIG. 18b is a sectional view taken along the line XVIIB—XVIIB of FIG. 18a;

FIG. 19 is a longitudinal cross section showing an eleventh embodiment of the ultrasonic endoscope according to the invention;

FIGS. 21a to 20g are cross sectional views cut along lines A—A to G—G.

DESCRIPTION OF THE PREFERRED EMBODIMENTS

The present invention will now be described with reference to the embodiments shown in the accompanying drawings.

Figure 1:
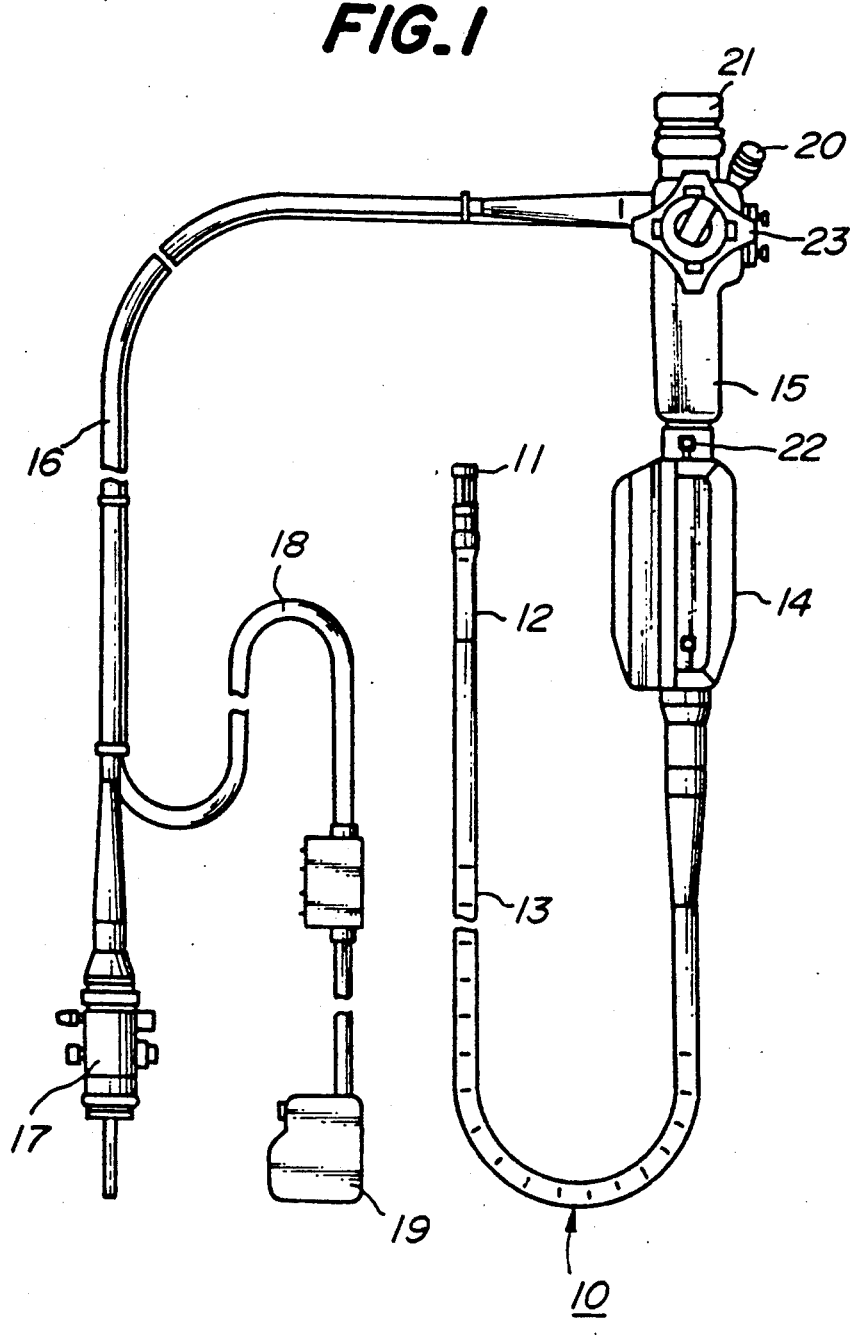
FIG. 1 is a front view of an ultrasonic endoscope apparatus to which a first embodiment of the present invention is applied.

FIG. 1 is an external side view of an ultrasonic endoscope apparatus to which a first embodiment of the present invention is applied.

As shown in FIG. 1, a probe 10 comprises a distal end 11, a bendable portion 12, and a flexible portion 13. A base portion of the probe 10 is connected to an ultrasonic operating portion 14 including a rotation mechanism for driving a rotor to rotate an ultrasonic vibrating unit. An endoscope operating portion 15 is connected to the ultrasonic operating portion 14 for controlling the bending of the bendable portion 12 of the probe 10, and to supply and suck air and liquid to and from the distal end 11. A universal cord 16 provided with an endoscope connector 17 and an electric cable cord 18 having an electric connector 19 are extended from the endoscope operating portion 15. An operating port 20 for inserting forceps into the probe 10, and an eyepiece 21 for optically observing an image obtained by an optical viewing system provided in the distal end 11, are attached to the endoscope operating portion 15. An injection opening 22 for injecting a deaerated liquid is formed in a portion connecting the endoscope operating portion 15 and the ultrasonic operating portion 14 with each other. A degree of bending of the bendable portion 12 is controlled by an angle knob 23 provided at the operating portion 15.

FIGS. 2a through 2h show parts of distal end 11.

Figure 2A:
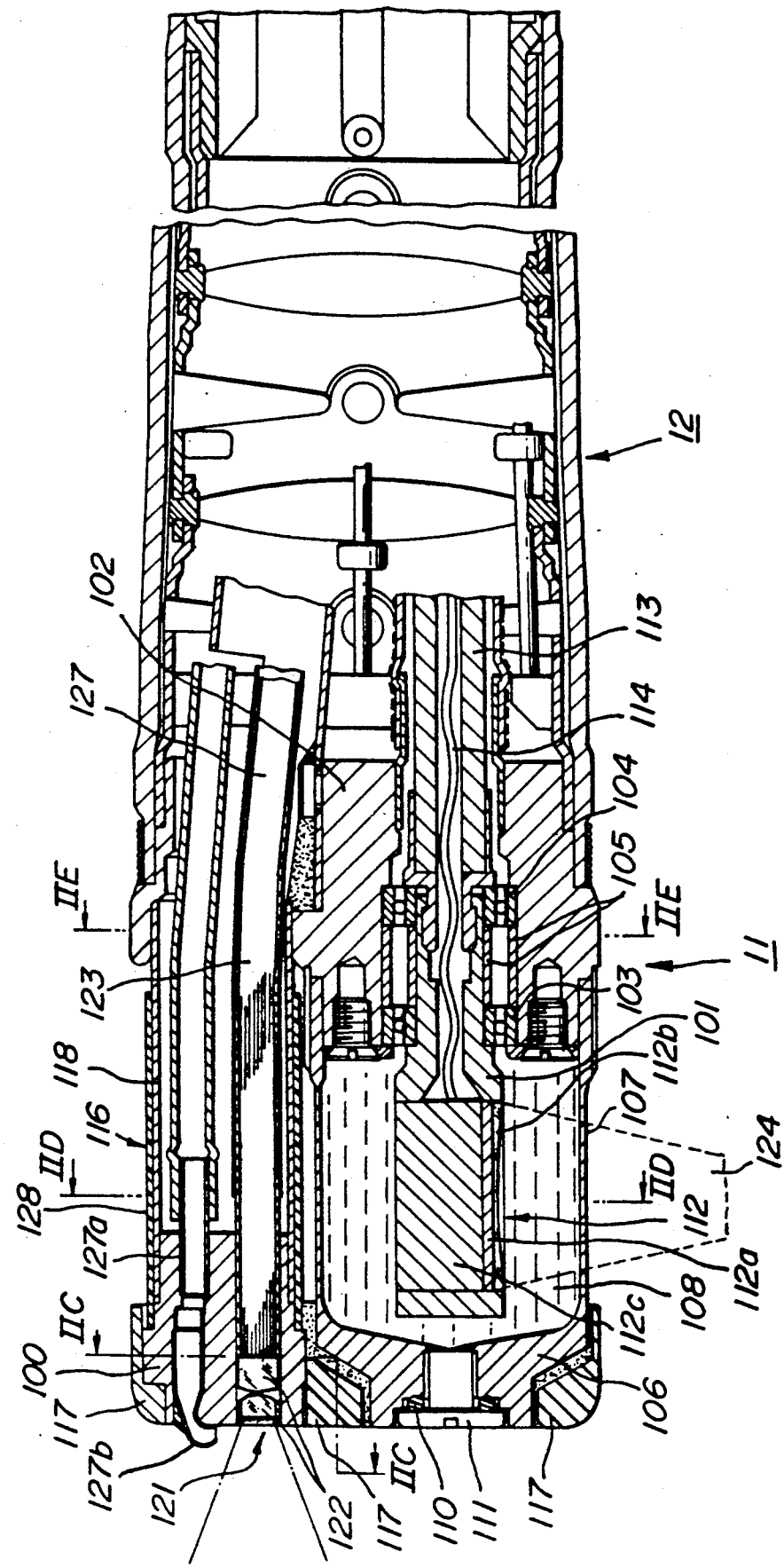
FIG. 2a is a sectional view of a main part of the first embodiment of the present invention.
Figure 2B:
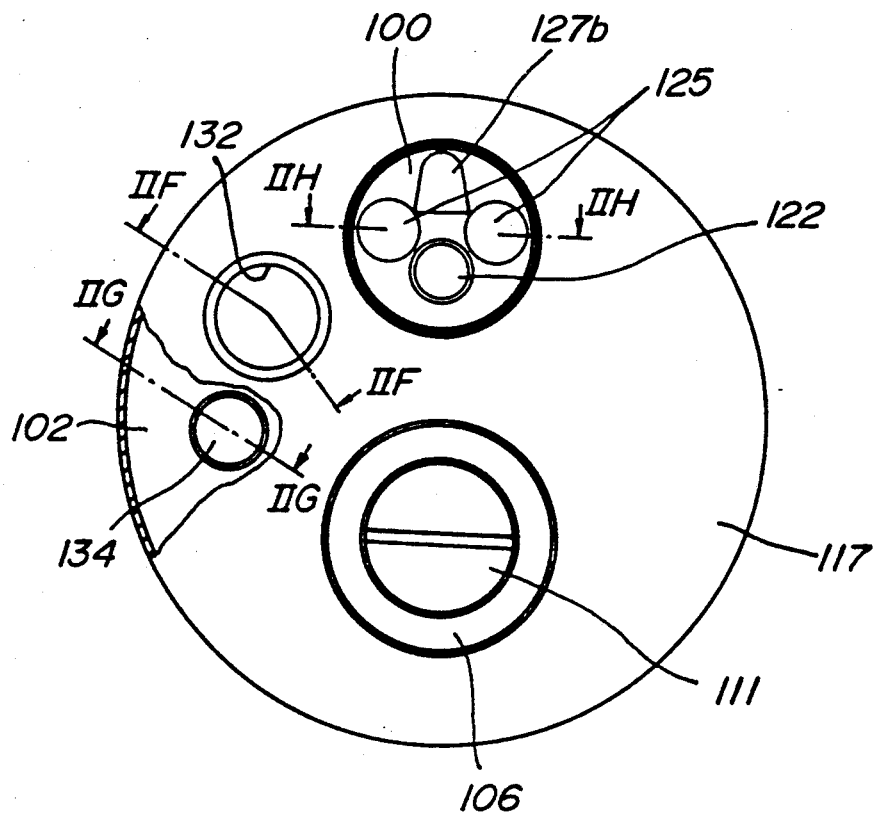
FIG. 2b is a front view of a distal end of a probe.
Figure 2C:
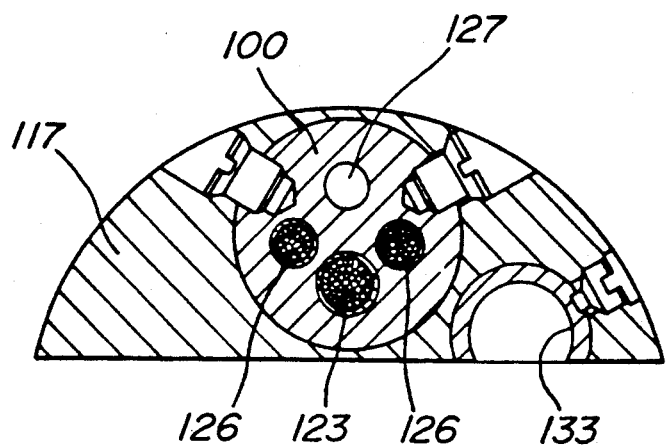
Figure 2D:
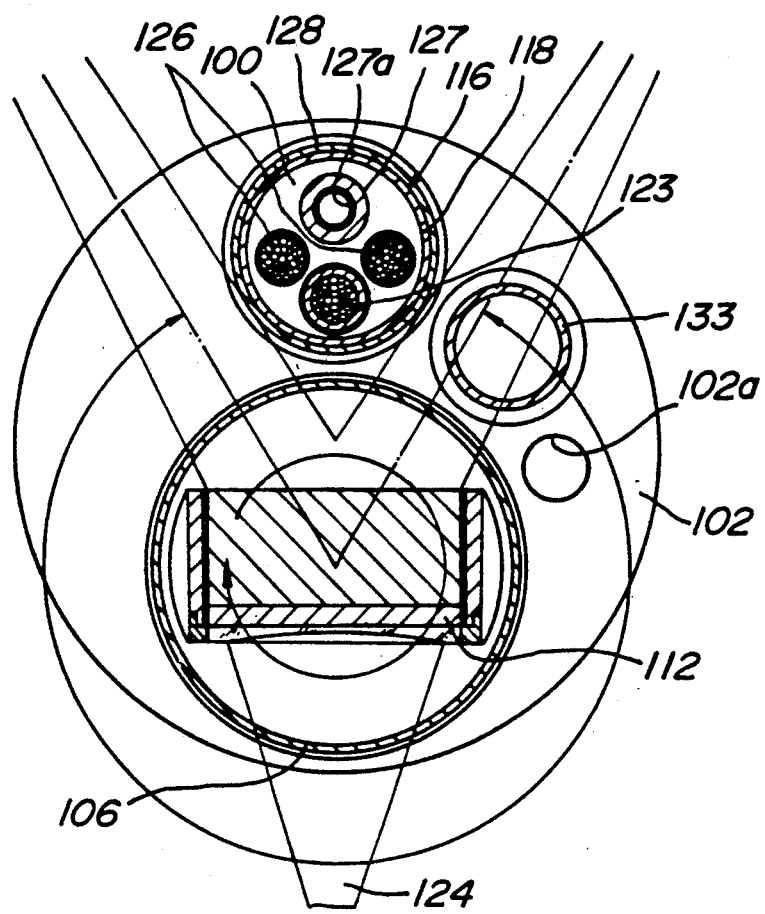
Figure 2E:
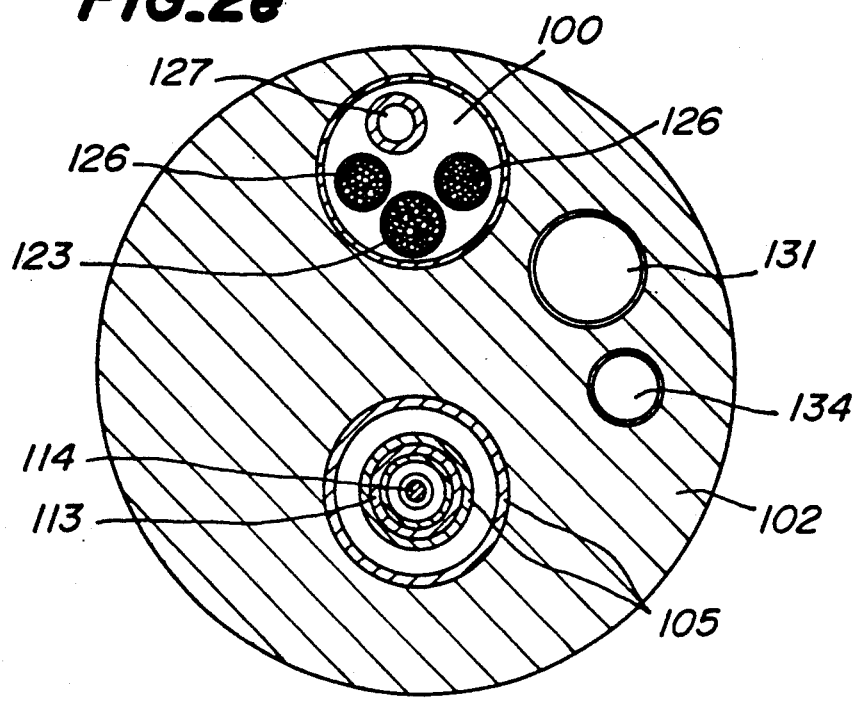
Figure 2F:
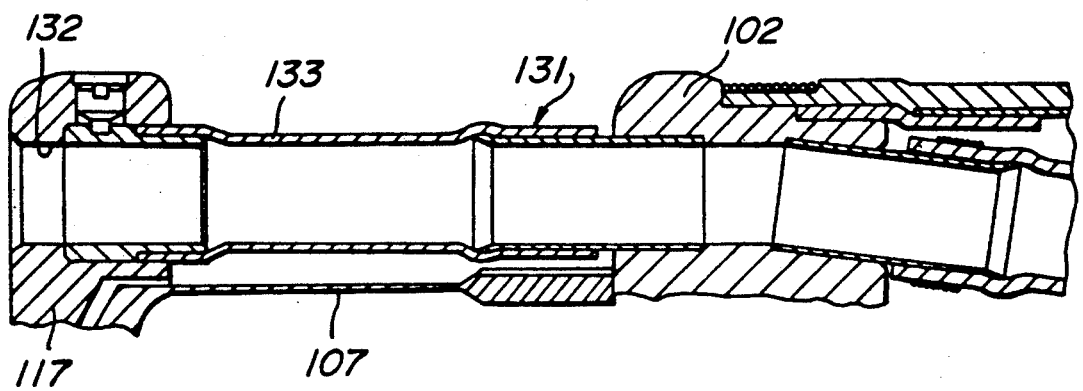
FIG. 2f is a sectional view taken along the line IIF—IIF of FIG. 2b.
Figure 2G:
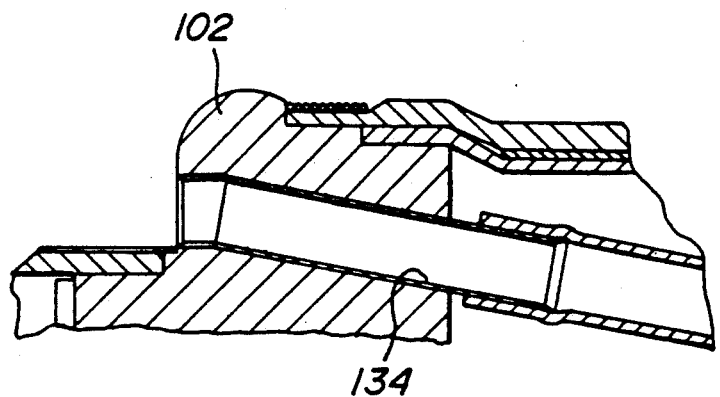
FIG. 2g is a sectional view taken along the line IIG—IIG of FIG. 2b.
Figure 2H:
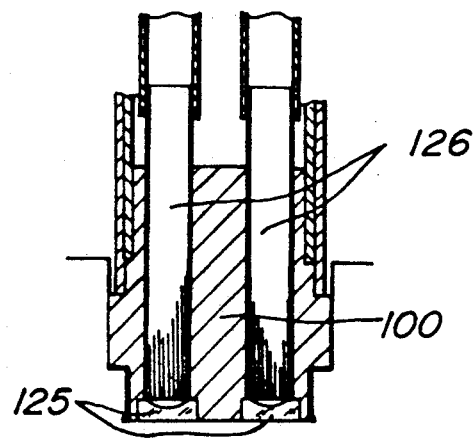
FIG. 2h is a sectional view taken along the line IIH—IIH of FIG. 2b.

As shown in FIG. 2a, a rotor 101 is rotatably supported by a distal end support member 102 through ball bearings 103 and 104 and a spacer 105. A cylindrical distal end cap 106 having an ultrasonic transmission window 107 formed therein is supported by a front end face of the distal end support member 102 such that the cap encloses the rotor 101. The distal end cap 106 is filled with an ultrasonic transmission medium liquid 108 which also serves as a lubricant. The end portion of the distal end cap 106 is closed by a seal member 110 and a seal screw 111 in a fluid-tight manner. An ultrasonic vibrating unit 112 including ultrasonic emitting and receiving element 112a, acoustic lens 112b wave absorbing member 112c, is fixed on the rotor 101, which is connected to a hollow flexible transmission cable 113 transmitting a rotative force of a motor (not shown) provided in the ultrasonic operating portion 14. A signal cable 114 connected to the ultrasonic vibrating unit 112 is led to the ultrasonic operating portion 14 through the transmission cable 113.

A cylindrical member 116 is provided between a front end of the ultrasonic support member 102 and a disc-like member 100 in parallel with the distal end cap 106, in such a manner that a front end face of the cylindrical member 116 is positioned in the same plane as a front end face of the distal end cap 106. The distal end support member 102 has a cylindrical shape and has a plurality of holes through which the distal end cap 106, the cylindrical member 116, and so on are passed. An end cover 117 is provided for covering the front end portions of the distal end cap 106, disc-like member 100 and the cylindrical member 116, and has substantially circular cross section.

The cylindrical member 116 is provided with an optical viewing system 121 having a frontward field of view composed of an objective lens 122, an image guide fiber 123, an optical illuminating system composed of illuminating lenses 125 and a light guide fiber 126, and an air and liquid supply tube 127. In an outer surface of a metal pipe 118 of the cylindrical member 116, at least a portion to which an ultrasonic beam 124 emitted from the ultrasonic vibrating unit 112 is projected is covered with a tube 128 of an elastomeric rubber having an ultrasonic absorption function, such as urethane rubber, silicon rubber, fluorine rubber, and the like, so that deterioration of an ultrasonic image due to the scattering of the ultrasonic beam by the cylindrical member 116 is prevented. The end of tube 127 is connected to a pipe 127a secured to the disc-like member 100 and the pipe 127a is further connected to a nozzle pipe 127b, so that the observation windows can be cleaned by projecting the liquid from the nozzle pipe.

A suction pipe 131 is arranged in parallel with the distal end cap 106 and the cylindrical member 116, and is connected to an opening 132 provided in the end cover 117. The pipe 131 is located adjacent to the ultrasonic transmission window 107. At least a portion of the pipe 131 through which an ultrasonic beam 124 is transmitted is formed by a tube 133 made of an elastomeric rubber, such as urethane rubber, neoprene rubber, and silicon rubber, having a high ultrasonic transmittance, and the pipe 131 is filled with a liquid such as water, whereby the ultrasonic beam 124 is effectively transmitted through the pipe 131. Therefore, the pipe 131 does not affect the ultrasonic image.

An opening 102a is formed in the distal end support member 102, and a deaerated liquid injecting pipe 134 for injecting a deaerated liquid serving as a medium for transmitting the ultrasonic beam is provided in this opening in parallel with the suction pipe 131. The bendable portion 12 and the flexible portion 13 (FIG. 1) are connected to a rear end portion of the distal end 11, to construct the probe 10.

Due to the construction of the first embodiment as described above, when an ultrasonic diagnosis is carried out, the probe 10 can be easily inserted into a body cavity such as large intestine and the gullet. Namely, the probe 10 can be inserted while confirming the direction of insertion by observation through the objective lens 122 provided at the front end face of the probe 10, and thus can be safely and easily guided to a desired portion. After the probe has reached the desired position, the deaerated liquid is injected into the body cavity through the deaerated liquid injecting pipe 134, and some of the liquid is sucked out again by means of the suction pipe 131, so that the body cavity is filled with the deaerated liquid. The rotor 101 and the ultrasonic vibrating unit 112 are then operated and an ultrasonic beam 124 is emitted and received in a radial direction perpendicular to the axis of the distal end support member 102, over a wide range except for the cylindrical member 116, and thus a desired ultrasonic laminagram image is displayed on a monitor of an observation device connected to the connector 19 (FIG. 1).

At this time, although a fan-shaped area corresponding to the cylindrical member 116 is dark, the other members do not disturb the transmission of the ultrasonic beam 124 therethrough, and thus a clear ultrasonic laminagram image is obtained over a wide scope of about 300 degrees. Further, in this first embodiment, since the end cover 117 is provided at the front end portion of the probe 10, the ultrasonic transmission window 107 is easily embedded in the transmission medium liquid, and since the end cover 117 has a round edge, the probe 10 can be inserted to and withdrawn from the body cavity without injuring an inner wall of the body cavity. Further, since the suction pipe 131 is arranged so as not to disturb the transmission of the ultrasonic beam therethrough, and the opening of the suction pipe 131 is provided adjacent to the observation window formed in the front end face of the probe 10, a forceps can be used in safety through the suction pipe 131. Still further, since this embodiment is constructed in such a manner that a deaerated liquid filling method is used in which a space for grooves for attaching balloons is not required, a length of the hard end portion of the distal end 11 can be shortened, and thus the probe can be further easily inserted into the body cavity.

Figure 3:
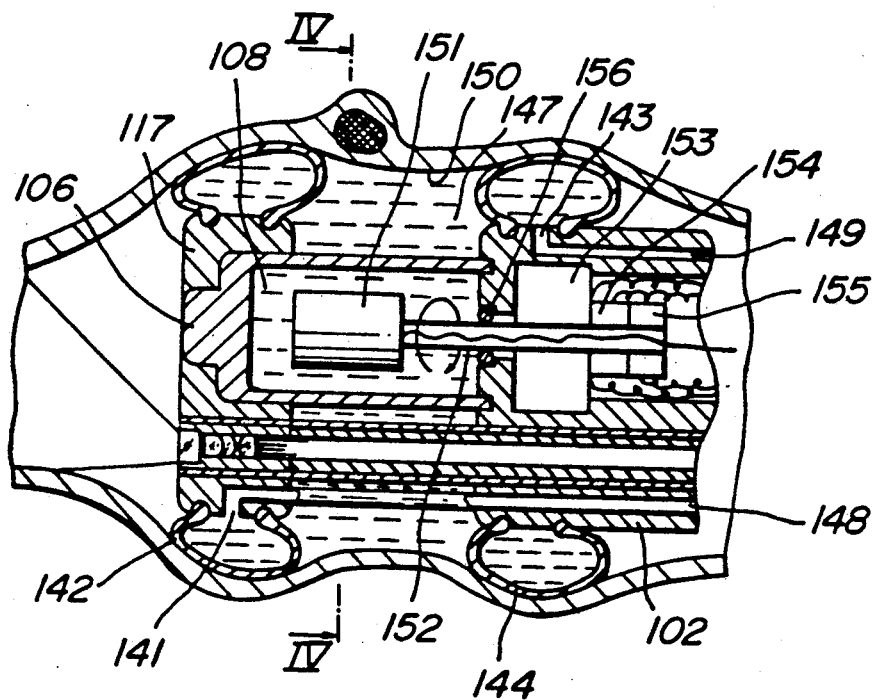
FIG. 3 is a sectional view showing a distal end of a second embodiment of the present invention.

FIG. 3 shows a second embodiment of the ultrasonic endoscope apparatus according to the present invention. In this drawing, parts the same as or corresponding to those of the first embodiment are denoted by the same reference numerals.

A first inlet and outlet port 141 for supplying air or liquid is formed in an outer surface of the end cover 117, and a first cylindrical balloon 142 is arranged to cover the first inlet and outlet port 141. Similarly, a second inlet and outlet port 143 is formed in an outer surface of the distal end support member 102, and a second cylindrical balloon 144 is provided to cover the second inlet and outlet port 143. An injection port 145 for injecting a deaerated liquid as a medium for transmitting an ultrasonic beam, and a suction port 146 for sucking out unwanted air and liquid are formed between the balloons 142 and 144, so that a cavity defined by these two balloons 142 and 144, and an inner wall 150 of the body cavity, is filled with the deaerated liquid 147. The inlet and outlet ports 141 and 143 are connected to an injection device such as a syringe provided in the operating portion 15, through injection pipes 148 and 149.

The ultrasonic vibrating unit 151 is connected to a rotatable shaft 152 to be rotated by a rotative force of a small ultrasonic motor 153, such as a ring type ultrasonic motor, provided in the distal end support member 102. An ultrasonic signal transmitting and receiving circuit 154 and a rotational position sensor 155 control a supply of a signal to the ultrasonic vibrating unit 112. A seal member 156 such as an O-ring is provided between a hole formed in the distal end support member 102 and the rotatable shaft 152, to seal the ultrasonic transmission medium liquid 108 in the distal end cap 106.

In the second embodiment as described above, in a body cavity which is difficult to be filled with the aerated liquid, such as a gullet, a large intestine, and the anus, first the air is injected into the balloons 142 and 144 located at the front and rear of the distal end cap 106, so that the balloons 142 and 144 are brought into tight contact with and press against the inner wall 150 of the body cavity. Then, the deaerated liquid 147 is injected through the injection port 145, while unwanted air is sucked through the suction port 147, so that the cavity between the balloons 142 and 144 is filled with the deaerated liquid, and accordingly, the ultrasonic diagnosis can be carried out without causing discomfort in the body cavity. Also, the view in front of the probe 10 during the insertion thereof can be observed, and thus the probe 10 can be easily and safety inserted.

Further, since the motor 153 and the rotational position sensor 155 are disposed in the distal end support member 102 in this second embodiment, a phase deviation generated due to a twisting of the transmission shaft 113 (FIG. 2a) is prevented, and thus a stable rotation of the ultrasonic vibrating unit is obtained. Still further, according to this second embodiment, a diameter of a portion of the probe 10 located at the rear of the distal end 11 can be reduced, and thus pain felt by the patient can be alleviated.

Figure 4:
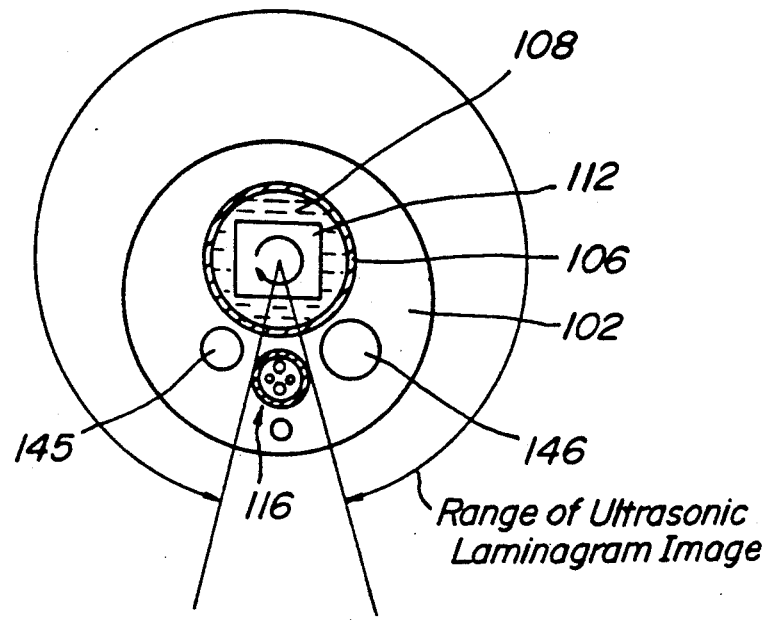
FIG. 4 is a sectional view taken along the line of FIG. 3.
Figure 5:
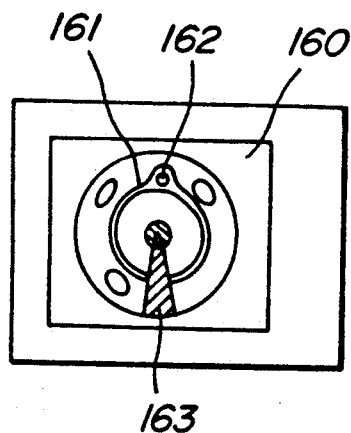
FIG. 5 is a schematic view showing an example of an ultrasonic laminagram image.

FIG. 4 is a sectional view taken along the line IV—IV of FIG. 3, and FIG. 5 is a representation of an ultrasonic laminagram image displayed on a monitor 160. As Shown in FIG. 5, a wall of a gullet 61 has a diseased portion 162, and although a dark part 63 is generated due to the interference of the cylindrical member 116 (FIG. 2a) with the wave, the diseased portion 162 of the wall of the gullet 61 can be fully observed.

Figure 6:
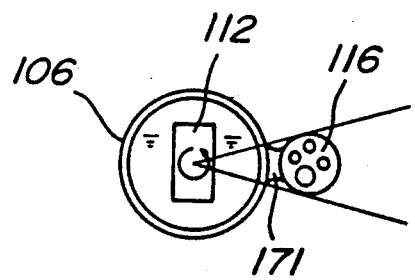
FIG. 6 is a sectional view showing a third embodiment of the present invention.

FIG. 6 shows a third embodiment of the present invention. In this embodiment, an acoustic absorption member 171 made of silicon rubber capable of absorbing an ultrasonic wave is provided between the distal end cap 106 and the cylindrical member 116, and the end cover 117 of the first embodiment is omitted. Therefore, the entry of impurities such as faces between the distal end cap 106 and the cylindrical member 116 is prevented, so that a rear portion of the cylindrical member 116 is clear of any acoustic absorption affect, and thus a disturbance of the ultrasonic image is reduced at a boundary of the non-affected portion and the ultrasonic image. Further, since the end cover 117 and disclike member 100 are not provided, the diameter of the distal end 11 is further reduced.

Figure 7:
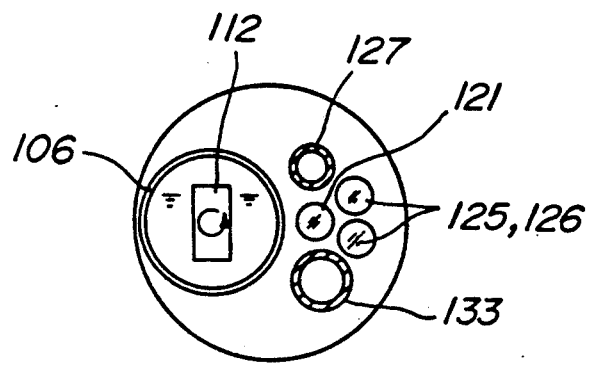
FIG. 7 is a sectional view showing a fourth embodiment of the present invention.

FIG. 7 shows a fourth embodiment of the present invention. The optical viewing system 121, the illuminating system 125, 126, and the air and liquid supply tube 127 provided in the cylindrical member 106 are arranged adjacent to the distal end cap 106 and in parallel with each other. Portions of the optical viewing system 121 and the optical illuminating system 24 to which an ultrasonic beam is applied are made of a plastic material, and the air and liquid supply tube 27 is made of an elastomeric rubber, so that a transmission of an ultrasonic beam therethrough is improved. Due to this construction, although the sensitivity of the apparatus is slightly lowered, an ultrasonic laminagram image can be obtained over a full scope of the compass, i.e., over 36 degrees.

Figure 8A:
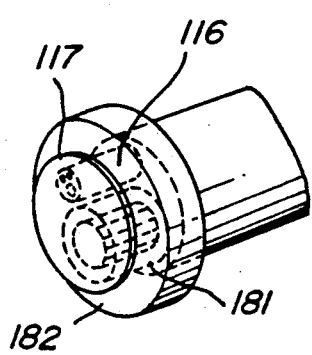
FIG. 8a is a perspective view of a fifth embodiment of the present invention.
Figure 8B:
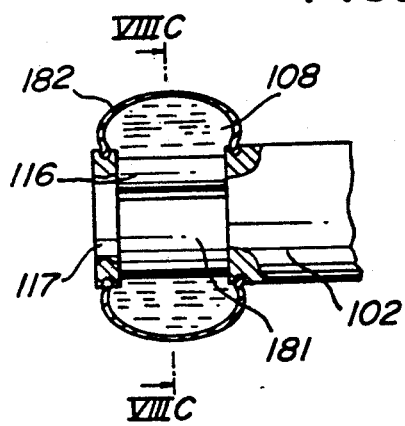
Figure 8C:
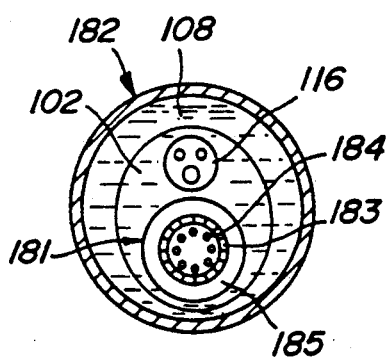
FIG. 8c is a sectional view taken along the line VIIIC—VIIIC of FIG. 8b.

FIGS. 8a through 8c show a fifth embodiment of the present invention. In this embodiment, the distal end cap 106 of the first embodiment is replaced by an electronic scan type ultrasonic vibrating unit 181 having a micro-convex or an electronic radial scan construction, so that an ultrasonic beam is emitted over almost the whole compass, a balloon 182 is provided to cover the whole vibrating unit 181, and deaerated liquid 2108 is filled in the balloon 182, i.e. the ultrasonic diagnosis is carried out by the balloon contact method. The ultrasonic vibrating unit 181 comprises an ultrasonic vibration element film 183 composed of a polymeric material or a compound material of a polymeric material and a ceramic, a plurality of signal cables 184, and an acoustic lens 185.

According to this fifth embodiment, since a motor, a rotational position sensor, and a rotational force transmitting mechanism are not required for driving the ultrasonic vibrating unit 181, the number of mechanical failures is decreased, and since bearings for the rotation mechanism are not required, the length of a hard portion provided at the distal end can be shortened, and thus it is easier to insert the probe 10 into the portion of the body to be examined.

Figure 9:
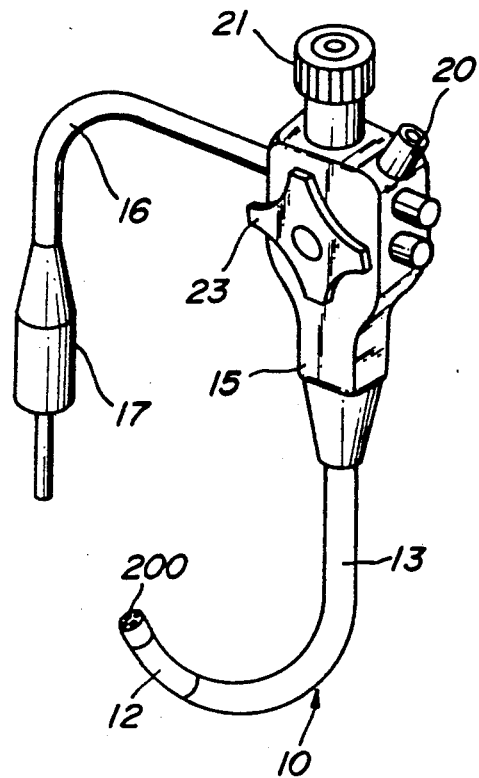
FIG. 9 is a perspective view of an ultrasonic endoscope apparatus to which sixth and seventh embodiments of the present invention are applied.

FIG. 9 shows an external view of an ultrasonic endoscope apparatus of a sixth embodiment of the present invention. As apparent from the drawing, the construction of the endoscope apparatus of FIG. 9 differs from that of the apparatus shown in FIG. 1 the ultrasonic operating portion 14 is not provided, and a tip member 200 is connected to the bendable portion 12. The remaining construction is the same as that shown in FIG. 1.

FIGS. 10 and 11 show the construction of a distal end of the sixth embodiment of the present invention.

The bendable portion 12 (FIG. 9) is provided with a bendable tube 201 constructed by connecting a plurality of bendable pieces 202 to each other in such a manner that the bendable pieces 202 can bend freely, and fitting a cylindrical member 203 formed of woven silk threads or stainless steel wire or an outer surface of the bendable tube 202, and fitting an elastic waterproof tube 204 made of rubber and the like on an outer surface of the member 203.

The front most bendable piece 202a is connected to the tip member 200 by an adhesive. The end portion of the elastic waterproof tube 204 is fixed to the tip member 200 by winding a thin wire 205 externally around the tip member 200. The thin wire 205 is then covered by an adhesive 206.

An image guide fiber 207, a light guide fiber 208, and a tool inserting channel 209 are extended in the probe 10 (FIG. 9).

One end of the image guide fiber 207 is connected to an objective lens 211 provided in an observation window 212 formed in the tip member 200, and the other end of the image guide fiber 207 is connected to the eyepiece 21 attached to an endoscope operating portion 15 (FIG. 9). Therefore, by looking through the eyepiece 21, the operator can observe a field of view in front of the probe 10 through the observation window 212.

One end of the light guide fiber 208 is connected to an illuminating lens 213 provided in an illumination window 214 formed in the tip member 200, and the other end of the light guide fiber 208 is connected to a light source (not shown) through a connector 17 fixed to the universal cord 16.

One end of the tool inserting channel 209 is led to a tool passing opening 215 formed in the tip member 200, and the other end of the tool inserting member 209 is communicated with a tool insertion opening 20 attached to the endoscope operating portion 15.

A cleansing nozzle 219 is arranged at the tip member 200 for cleaning the observation window 212.

The image guide fiber 207 is constructed by covering a fiber bundle 207a with an outer tube 207b. A sleeve 207c fixed to the end portion of the tube 207b is fitted in the observation window 212 formed in the tip member 11, and is fixed to the window 212 by an adhesive. The light guide fiber 208 is constructed by covering a fiber bundle 208a with an outer tube 208b. A sleeve 208c fixed to the end portion of the tube 208b is fitted and adhered to the illumination window 214 formed in the tip member 200.

The image guide fiber 207 and the light guide fiber 208 are inserted in a single protection tube 221. Namely, the fibers 207 and 208 are bundled together and covered by one protection tube 221, which is a cylindrical flexible tube and is longer than the bendable portion 12. The end portion of the protection tube 221 is connected to the tip member 200 by a plurality of pins 222.

The operation of this sixth embodiment is described below.

When the angle knob 23 of the endoscope operating portion 15 is turned, the bendable portion 12 is bent, and accordingly, the tip member 200 is turned in a different direction. Namely, the scanning through the observation window 212 is carried out by remote control.

This bending operation causes a bending of the members such as the image guide fiber 207, the light guide fiber 208, and the tool inserting channel 209, and therefore, the image guide fiber 207 and the light guide fiber 208 come into contact with each other, and in contact with the tool inserting channel 209 or the bent tube 201, and are deformed. The image guide fiber 207 and the light guide fiber 208, however, are covered by the protection tube 221, and thus these fibers 207 and 208 cannot come into contact with the other members, and therefore are not deformed by contact with these other members. Namely, damage to the fibers 207 and 208 is prevented.

Further, since the fiber bundle 207a and 208a are covered by the outer tubes 207b and 208b, respectively, damage to these fiber bundles 207a and 208a is also prevented, and thus the durability and operation life of the fibers 207 and 208 is prolonged.

Further, since the image guide fiber 207 and the light guide fiber 208 are covered by the single protection tube 221, the diameters of the fibers 207 and 208 can be reduced, in comparison with a conventional construction in which each fiber is separately covered by a protection tube, so that the space required for installation of the fibers 207 and 208 is reduced, and thus the probe 10 can be made more slender and accordingly, is more easily inserted into a body cavity, thereby reducing the pain felt by a patient.

Figure 13:
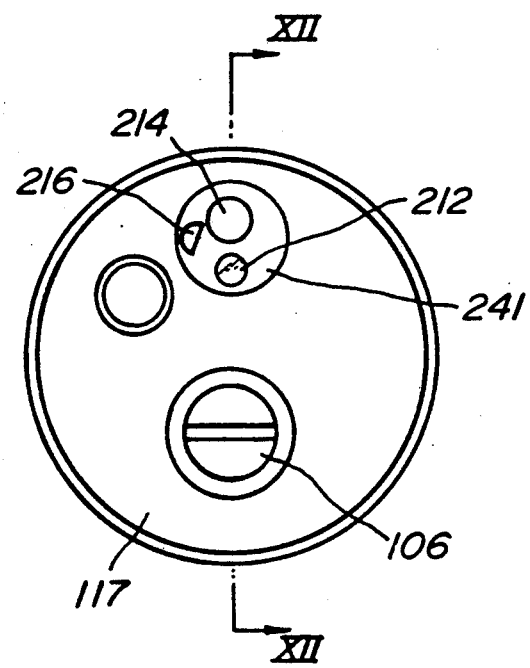
FIG. 13 is a front view of a distal end of a probe of the seventh embodiment of the present invention.
Figure 14:
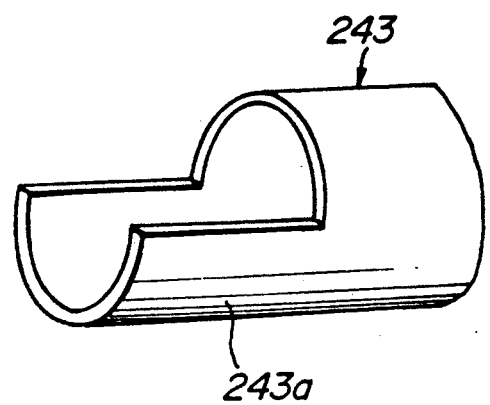
FIG. 14 is a perspective view of a protection tube.

FIGS. 12 through 14 show a seventh embodiment of the present invention which is applied to a scanning type ultrasonic endoscope apparatus.

This apparatus comprises an ultrasonic search unit 112 provided at the tip member 200. The ultrasonic vibrating unit 112 is rotatably supported by the tip member 200 through bearings 231 and 232, and projects from a front end face of the tip member 200. The ultrasonic vibrating unit 112 is enclosed by a distal end cap 107 fixed to the tip member 200.

The ultrasonic vibrating unit 112 is connected to a joint 233 supported by the bearings 231 and 232, and the joint 233 is connected to a hollow shaft 234, in which a signal cable 235 connected to the ultrasonic search unit 112 is extended and led to the operating portion 15 (FIG. 9).

The hollow shaft 234 is extended in a guide tube 236. The interior spaces of the guide tube 236 and the distal end cap 106 are filled with a liquid having a low ultrasonic damping affect and approximately the same acoustic impedance as the distal end cap 106.

A cylindrical member 116 is connected to a front end face of the tip member 200, and a frame 241 is connected to an end portion of the cylindrical member 116. As in the sixth embodiment, an observation window 212, an illuminating window 214, and a cleansing nozzle 216 are provided in the frame 241.

An image guide fiber 207 is connected to an objective lens 211 provided in the observation window 212, and light guide fiber 208 is connected to an illumination lens 213 provided in the illumination window 214. An air and liquid supply tube (not shown) is connected to the cleansing nozzle 216.

A construction in which the image guide fiber 207 and the illumination fiber 208 are connected to the frame 241 may be the same as that in which the fibers are connected to the tip member 200, and for this purpose, the tip member 200 is provided with a hole 242 through which the image guide fiber 207, the illuminating fiber 208, and the air and liquid supply tube are extended.

A protection tube 243 covering the image guide fiber 207 and the illuminating fiber 208 as a bundle is connected to the rear end portion of the tip member 200.

The projection tube 243 is a cylindrical flexible tube, and is longer than the bendable portion 12. A semicylindrical projecting portion 243a is formed on the end portion of the protection tube 243, as shown in FIG. 14, and is fixed to the tip member 200 by a screw 244 or an adhesive, as shown in FIG. 12

The cylindrical member 106 enclosing the ultrasonic vibrating unit 112 and the frame 241 is covered by an end cover 117 in a fluid tight manner. A balloon 245 made of a cylindrical flexible material is provided in such a manner that one peripheral end of the balloon 245 is connected to the end cover 117, and the other peripheral end of the balloon 245 is connected to the tip member 200. Namely, the front end portion of the balloon 245 is provided with a front engaging portion 245a such as an O-ring, and the rear end portion of the balloon 245 is also provided with a rear engaging portion 245b such as an O-ring. The front engaging portion 245a is engaged with a groove 246 formed on an outer surface of the end cover 117, and the rear engaging portion 245b is engaged with a groove 247 formed on an outer surface of the tip member 200.

Water or air is injected into the balloon 245 through a opening (not shown) provided at the tip member 200.

A tool insertion opening 248 is provided in the end cover 117.

In this construction, since the image guide fiber 207 and the illuminating fiber 208 are covered by the protection tube 243, these fibers 207 and 208 cannot come into contact with the other members, and thus deformation of these fibers 207 and 208 is reduced.

In the seventh embodiment, the hollow shaft 234 is made of a hard material, and therefore, if the image guide fiber 207 and the illuminating fiber 208 come into contact with the hollow shaft 234, these fibers 207 and 208 may be subjected to a strong deformation force, but damage to these fibers 207 and 208 will not occur because they are covered by the protection tube 243, and accordingly, the durability and operating life of the image tube guide fiber 207 and the illuminating fiber 208 are extended.

Further, since the image guide fiber 207 and the illuminating fiber 208 are covered by the single protection cover 243, the space required for housing the fibers 207 and 208 is reduced, and thus the diameter of the probe 10 (see FIG. 9) is reduced. As a result, the probe is more easily inserted into a body cavity, and the pain felt by a patient is reduced.

Still further, in this embodiment, since the balloon 245 is provided to cover the portion between the end cover 117 and the tip member 200, a recess is not formed between the end cover 117 and the tip member 200, and thus impurities cannot enter that portion and adhere to the distal end cap 106 or the cylindrical member 116.

FIGS. 15, 16a, 16b, and 16c show an eighth embodiment of the present invention.

Figure 15:
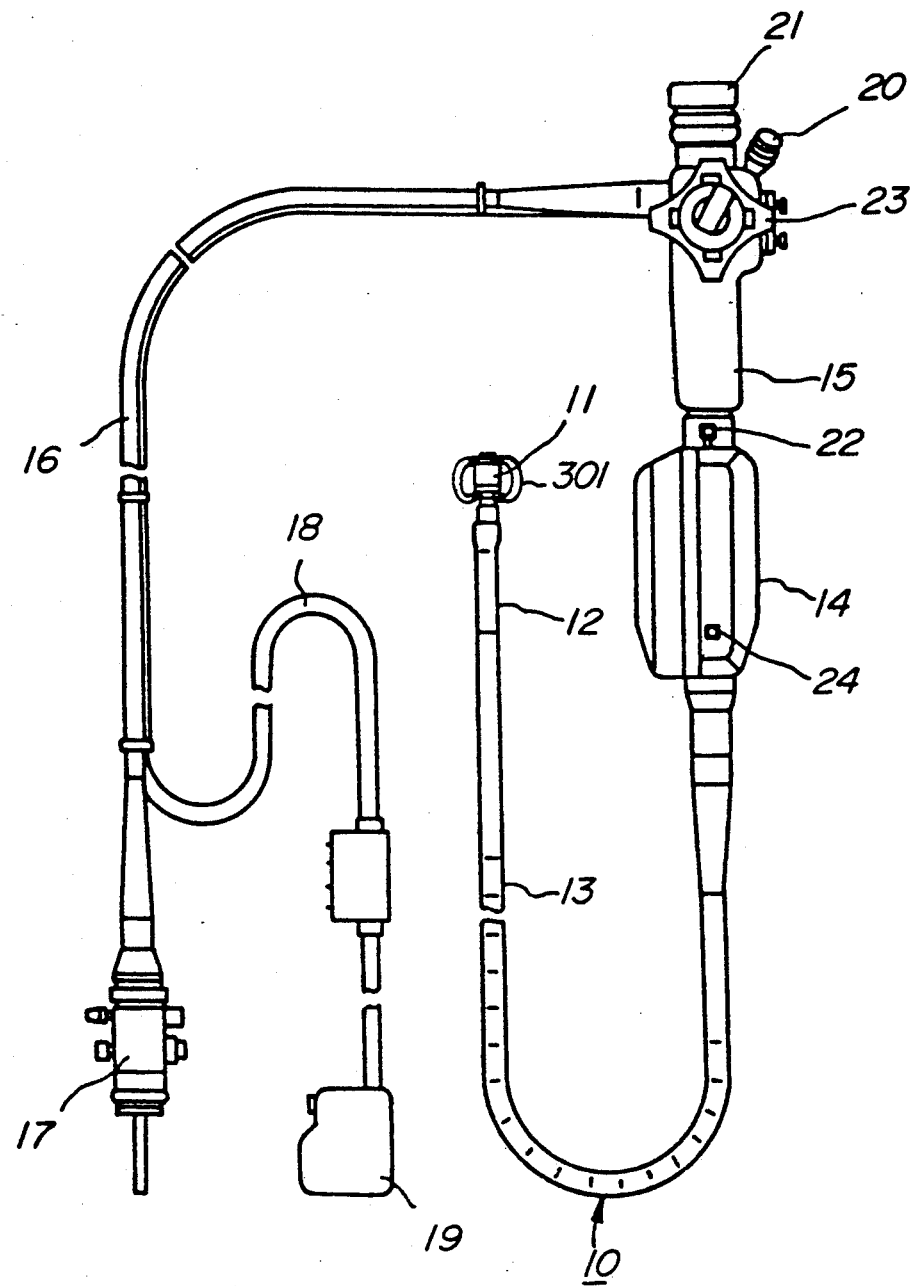
FIG. 15 is a perspective view of an ultrasonic endoscope apparatus to which the eighth through tenth embodiments of the present invention are applied.

FIG. 15 shows an external side view of an ultrasonic endoscope apparatus to which this eighth embodiment is applied. This apparatus is provided with a balloon 301 on the distal end 11 of the probe 10, and a cock 24 for discharging deaerated liquid in the balloon 301 outside of the apparatus and sucking cleansing liquid into the distal end through a tool insertion channel. The remaining construction is the same as that of the first embodiment.

Figure 16A:
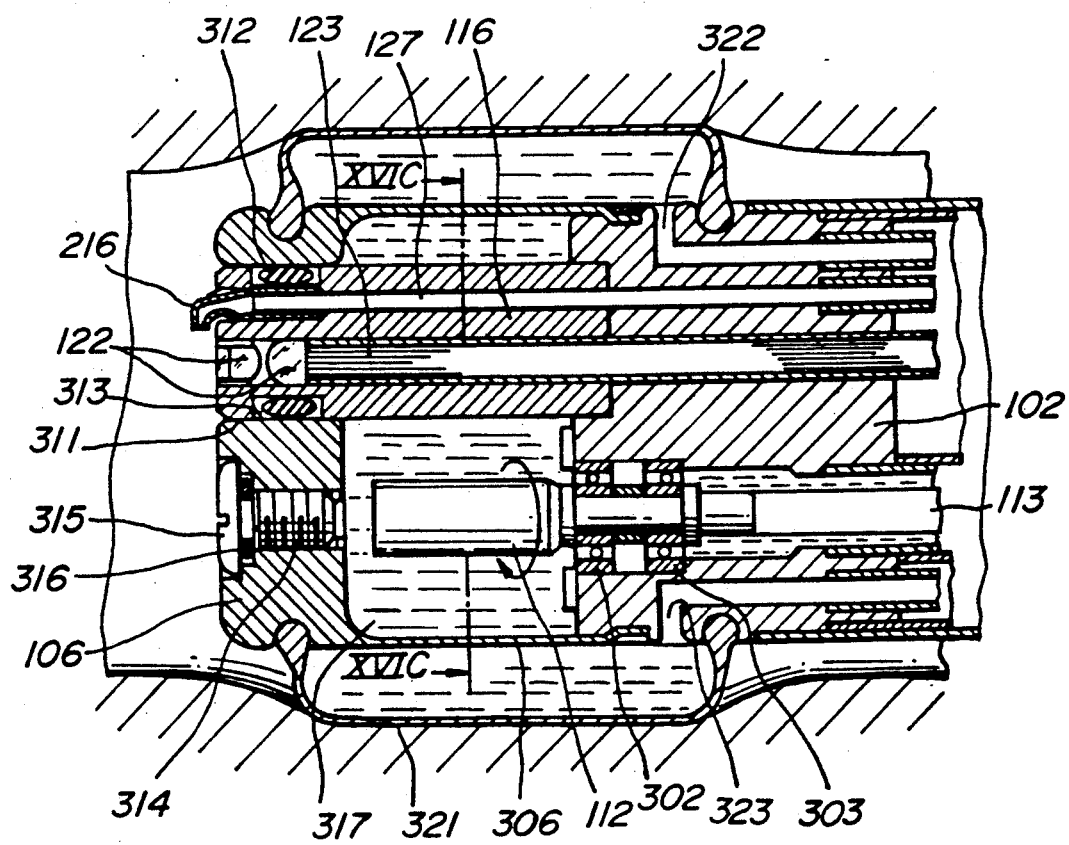
FIG. 16a is a sectional view of a distal end of the eighth embodiment of the present invention.
Figure 16B:
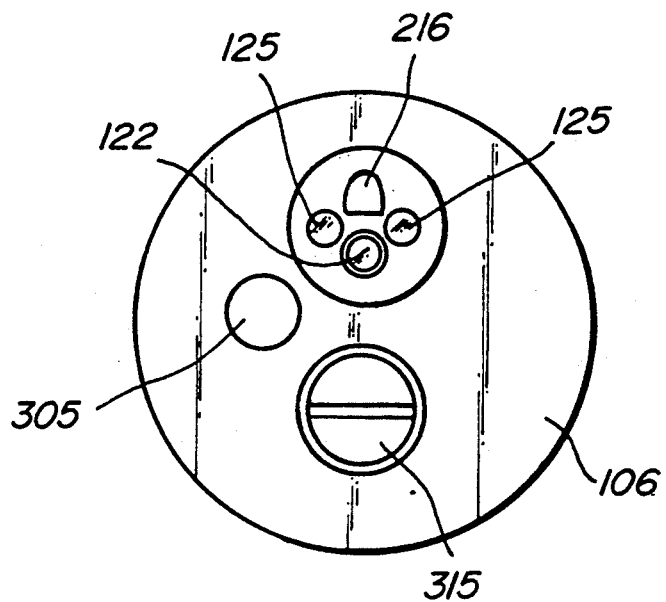
Figure 16C:
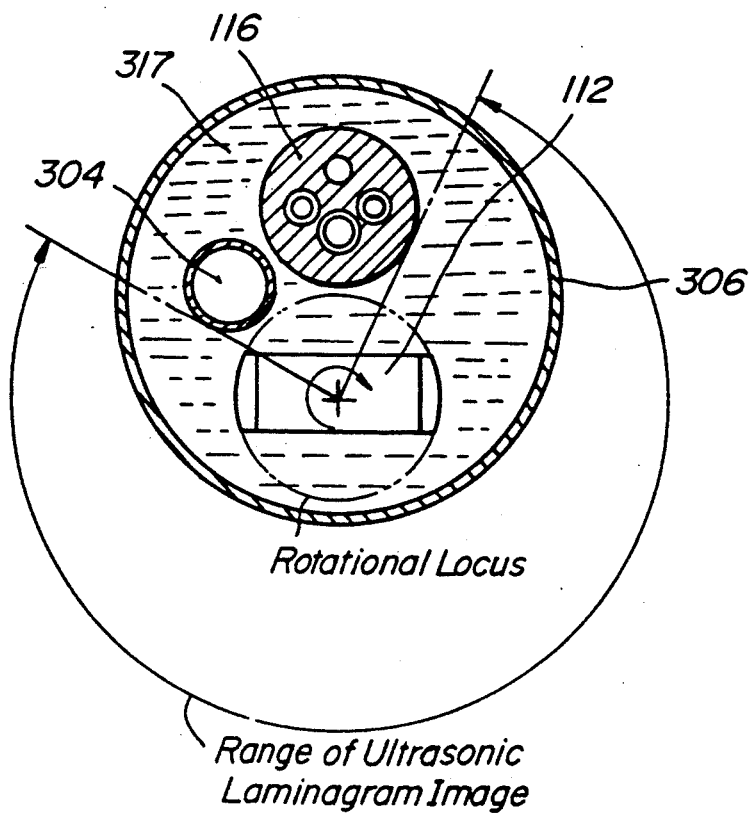

FIGS. 16a through 16c show a construction of the internal part of the distal end 11 wherein an ultrasonic vibrating unit 112 is rotatably supported by bearings 302 and 303 in a distal end support member 102 made of a hard material. A flexible hollow shaft 113 is connected to a rotor for rotating the ultrasonic vibrating unit 112 to transmit a rotative force of a rotation drive mechanism provided in the ultrasonic operating portion 14, to the ultrasonic vibrating unit 112. A cylindrical support member 116 including an optical observation system is provided adjacent to the ultrasonic search unit 112, and is fixed to the distal end support member 102.

Preferably, the cylindrical support member 116 is separated from the ultrasonic search unit 112 by a locus of rotation of the unit 112, and is located as close as possible to the ultrasonic vibrating unit 112, to reduce the diameter of the distal end 11 of the probe 10. Further, preferably the diameter of the cylindrical support member 116 is smaller than or equal to the rotational locus of the ultrasonic vibrating unit 112, and is set in such a manner that the ultrasonic vibrating unit 112 can scan as wide a fan shape as possible.

A suction channel 304 composed of a tube made of a material having a good ultrasonic beam transmission such as an urethane rubber is provided adjacent to the ultrasonic search unit 112 and the cylindrical support member 116, and is connected to an opening 305 formed in a distal end cap 106.

The distal end cap 106 is provided with a cylindrical cover 306 formed integrally therewith. The cylindrical cover 306 has the same diameter as the distal end support member 102 and completely encloses the ultrasonic vibrating unit 112, the cylindrical support member 116, and the suction channel 304. The cylindrical cover 306 is extended and connected to the distal end support member 102.

The distal end cap 106 is provided with a fitting hole 311 in which the end portion of the cylindrical support member 116 is fitted in such a manner that the front end face of the cylindrical support member 116 and the front end face of the distal end cap 106 are positioned in the same plane. A seal member 312 such as an O-ring is arranged at the front end portion of the cylindrical support member 116 to maintain a water-tight fitting between an inner wall 313 of the fitting hole 311 and the cylindrical support member 116. The distal end cap 106 is provided with a threaded hole 314 for injecting an ultrasonic transmission medium liquid into the distal end cap 106. The threaded hole 314 is closed by a plug 315 and sealed by a seal ring 316 such as an O-ring. An ultrasonic transmission medium 317 such as a deaeration liquid having a low ultrasonic beam damping ratio is filled in the distal end cap 106.

The cylindrical support member 116 includes an optical observation system, an optical illumination system, and a nozzle 216. The optical observation system is composed of objective lenses 122 having a field of view which covers a direction in which the probe 10 is to be inserted, and an image guide fiber 123. The optical illumination system is composed of illumination lenses 125 and a light guide fiber. The nozzle 216 is communicated with an air and liquid supply tube 127.

A cylindrical balloon 321 is provided to completely enclose the cylindrical cover 306, and the distal end support member 102 is provided with an injection port 322 and a suction port 323 opening into the interior of the balloon 321. A part of the cylindrical cover 306 through which an ultrasonic beam is transmitted is made of material having a high ultrasonic beam transmission property, such as polyethylene.

When a body cavity is to be examined by this ultrasonic endoscope apparatus, the probe 10 is inserted into an internal organ such as such as the large intestine or gullet in the body cavity. At this time, since the operator can insert the probe 10 into the body cavity while observing the direction of insertion, the probe 10 can be inserted and reach a desired position safely and easily. When the probe 10 reaches the desired position, an ultrasonic transmission medium liquid such as a deaeration liquid is injected into the balloon 321 through the injection port 322, and thus the balloon 321 is forced into tight contact with an inner wall of the body cavity.

In accordance with an object of the diagnosis and the portion examined, the balloon 321 may be removed and the internal organs to be examined may be filled with the ultrasonic transmission medium liquid. In this case, the ultrasonic vibrating unit 112 is driven so that an ultrasonic beam is emitted and received in a radial direction perpendicular to the axis of the probe 10, and completely around the axis, to carry out a scan and display an ultrasonic image on a monitor of the ultrasonic observation apparatus. In the displayed observation image, although a fan-shaped portion extending over 60 through 90 degrees, corresponding to the cylindrical support member 116 and the suction channel 304, cannot be observed, the remaining portion extending over 270 through 300 degrees can be clearly displayed as the ultrasonic laminagram image.

According to this embodiment, because the field of view in front of the probe 10 can be observed, the probe 10 can be easily inserted into a bent portion of the body cavity, and safely reach the desired position. Further, during the examination by an ultrasonic scan, the scanning can be carried out over a wide range, and since the support member 116 has an approximately cylindrical shape, little deterioration of the reception of the reflected ultrasonic beam occurs, and thus a clear ultrasonic image can be obtained without noise.

Further, since the distal end cap 106 including the cylindrical cover 306 is formed by a hard material having a high ultrasonic transmission property, such as polyethylene, and is smoothly connected to the distal end support member 102, the distal end of the probe 10 will not damage a mucous membrane in a body cavity, and impurities will not accumulate on the distal end 11. Further, because a portion by which the cylindrical support member 116 is fitted to the distal end cap 106 is closed by the seal member 312 in a fluid tight manner, if the distal end cap 106 is damaged, only the cap 106 must be replaced.

Figure 17:
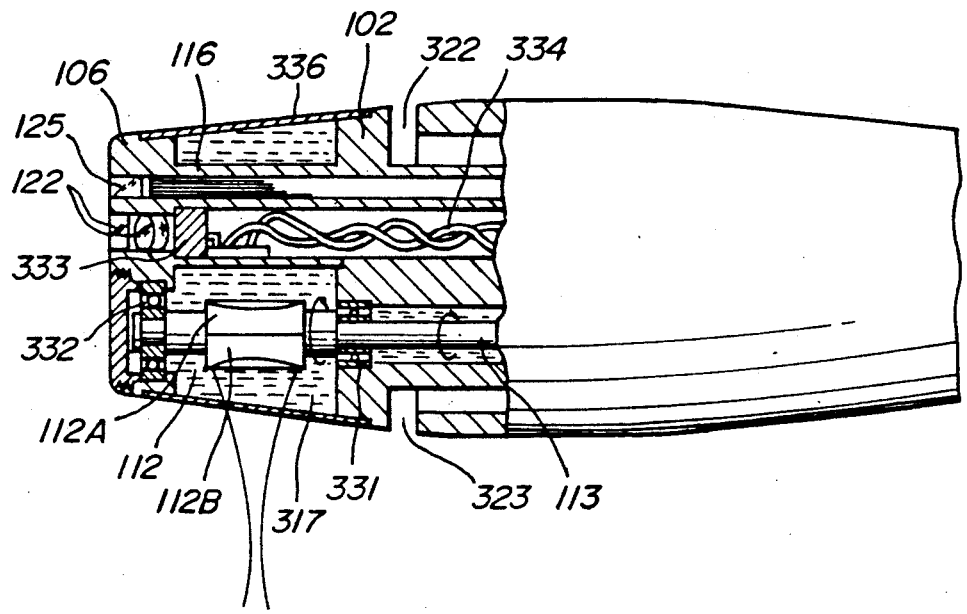
FIG. 17 is a sectional view of the ninth embodiment of the present invention.

FIG. 17 shows a ninth embodiment of the present invention. In this embodiment, the ultrasonic vibrating unit 112 is constructed by fixing an ultrasonic search element 112A to a surface of another ultrasonic vibrating element 112B, these elements 112A and 112B having different frequencies and different acoustic characteristics. This ultrasonic vibrating unit 112 is rotatably supported by the distal end support member 102 and the distal end cap 106 through bearings 331 and 332. The optical observation system comprises a solid state image pickup element 333 such as a CCD and a signal cable 334, instead of the image guide fiber 123 of the eighth embodiment. An image obtained by the element 333 is transmitted to a video processor to be displayed on a monitor.

Further, in this embodiment, a connecting cover 336 is formed separately from the distal end cap 106, and has a shape which diverges toward the distal end support member 102, i.e., has the shape of a truncated cone. Namely, the distal end support member 102 has a larger diameter than the distal end cap 106, and the distal end support member 102 and the distal end cap 106 are connected by the connecting cover 336 so that a portion between the distal end cap 106 and the distal end support member 102 is covered by the connecting cover 336. In this embodiment, a balloon is not provided.

According to this ninth embodiment, since the distal end has a tapered or truncated cone shape, the insertion of the probe 10 into a body cavity is smoother, and since in this optical observing system an image is displayed on a monitor with the aid of the CCD 333, the operator can insert the probe into the body cavity while viewing the image displayed on a monitor. Further, since an optical image can be displayed on the monitor, it becomes easier to carry out an endoscope diagnosis of a diseased portion of a body cavity.

Figure 18A:
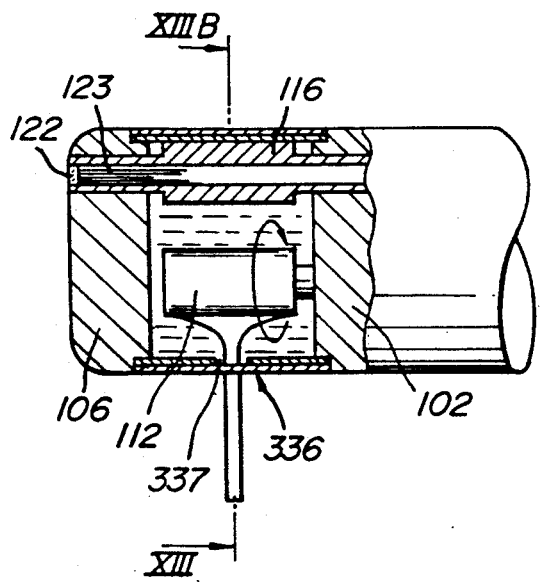
FIG. 18a is a sectional view of a distal end of the tenth embodiment of the present invention.
Figure 18B:
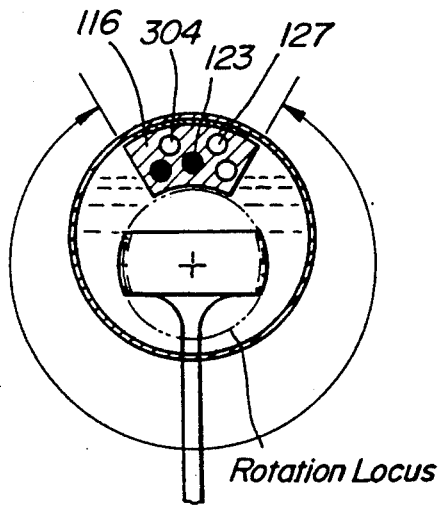

FIGS. 18a and 18b show a tenth embodiment of the present invention. In this embodiment, a cylindrical connecting cover 336 is provided with an inner cover 336a and an outer cover 336b. The inner cover 336a is made of a hard plastic material and provided with a slit-like passage 337 having such a width that an ultrasonic beam can pass therethrough. The outer cover 336b is made of a material having a high ultrasonic transmission property and having a low reflective property, such as a urethane rubber or a silicon rubber. Also since the cover 336 has a double construction composed of the inner and outer covers 336a and 336b, any deterioration of the ultrasonic image due to multiple echoes from the cover is substantially prevented. Further, since the breadth of the passage 337 need be only 2 to 3 mm, which is slightly larger than the breadth of the ultrasonic beam, even if the passage 337 is covered by an elastomeric material such as urethane rubber, perforation of the portion corresponding to the passage 337 or damage by deformation caused when the probe 10 is inserted into a body cavity, is substantially prevented.

Further, in this embodiment, the cylindrical support member 116 has a fan-shape in which a section is diverged from the rotational center of the ultrasonic vibrating unit 112, and therefore, a portion in which an ultrasonic image cannot be observed is reduced, and the distal end 11 of the probe 10 can house more members than a distal end 11 in which the cylindrical support member has a round shape.

Figure 20:
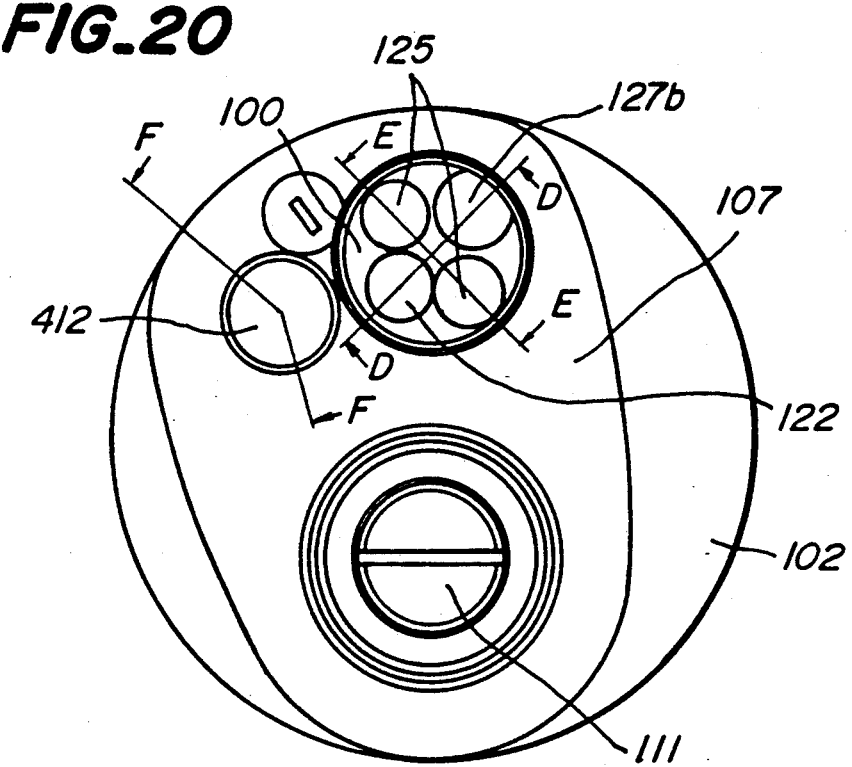
FIG. 20 is a front view of the endoscope shown in FIG. 19.
Figure 21A:
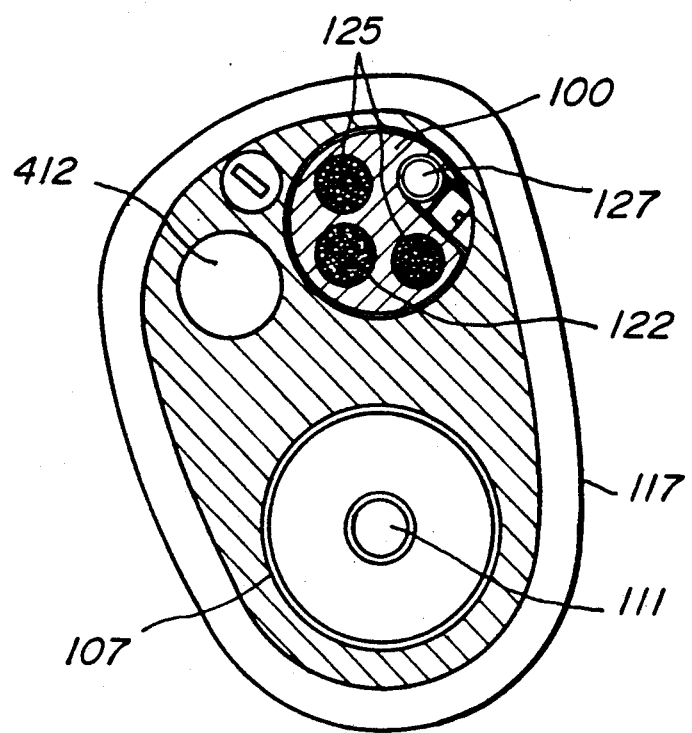
Figure 21B:
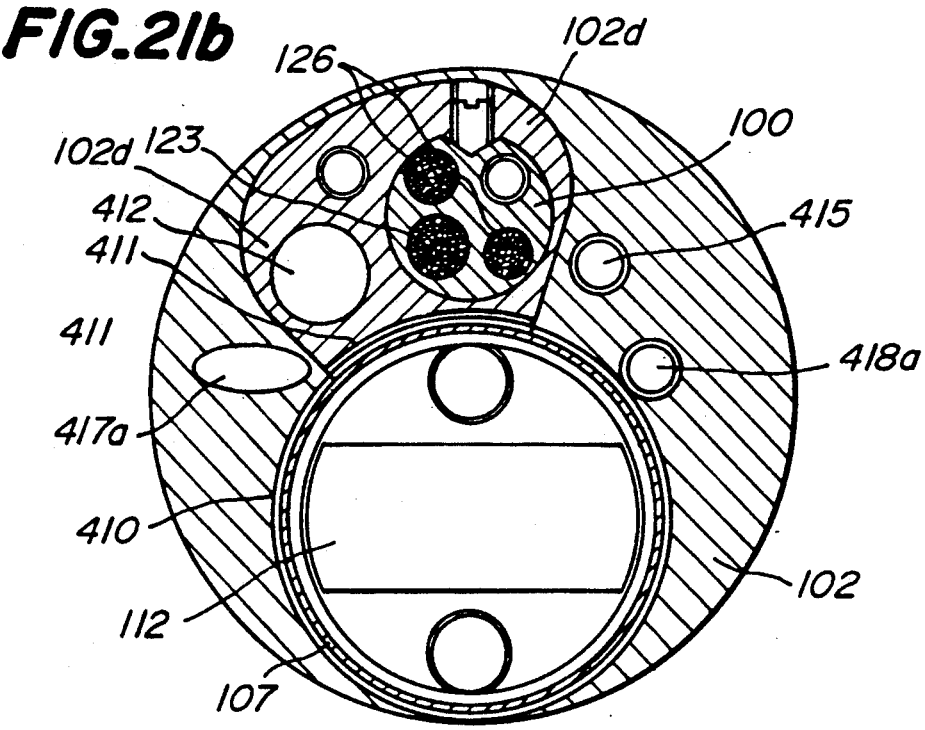
Figure 21C:
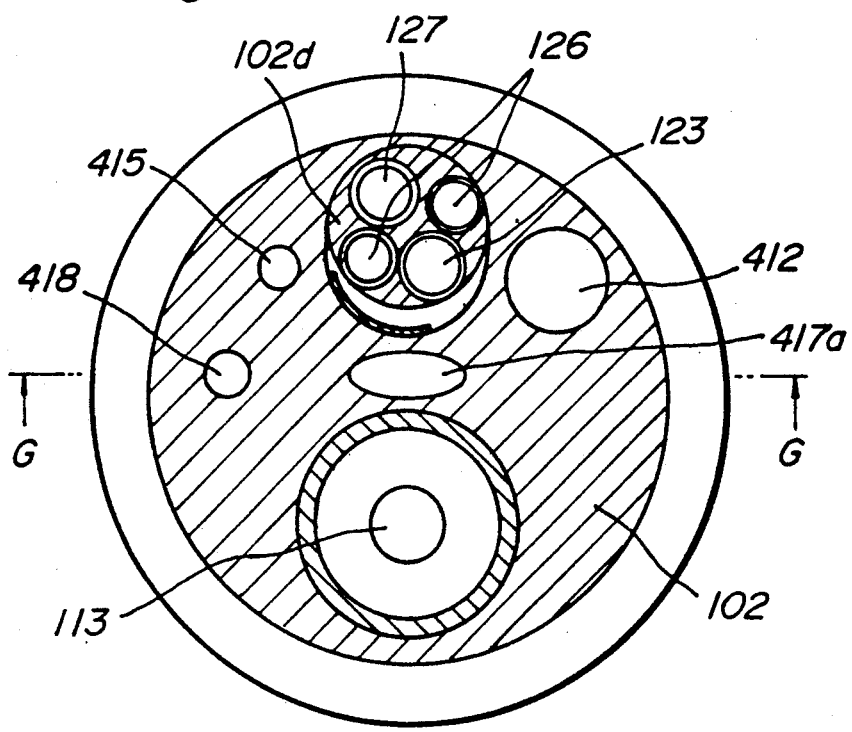
Figure 21D:
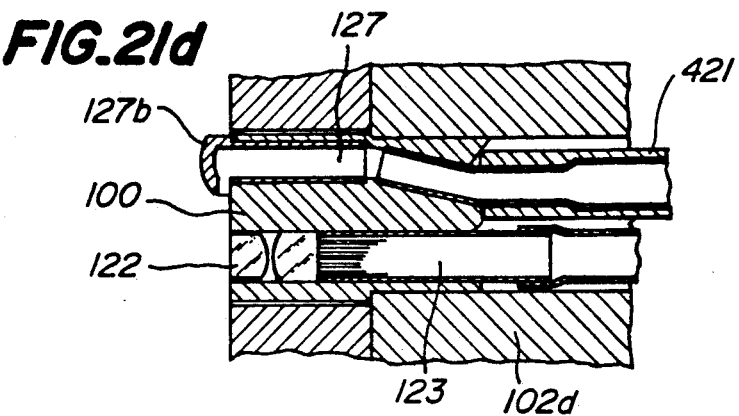
Figure 21E:
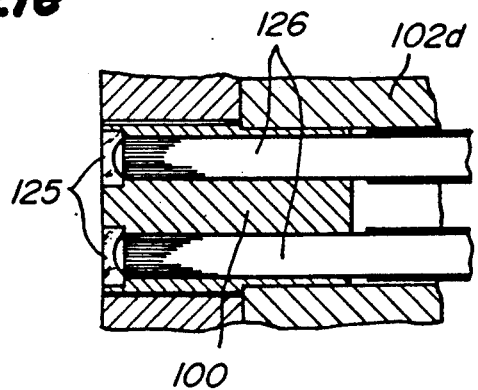
Figure 21F:
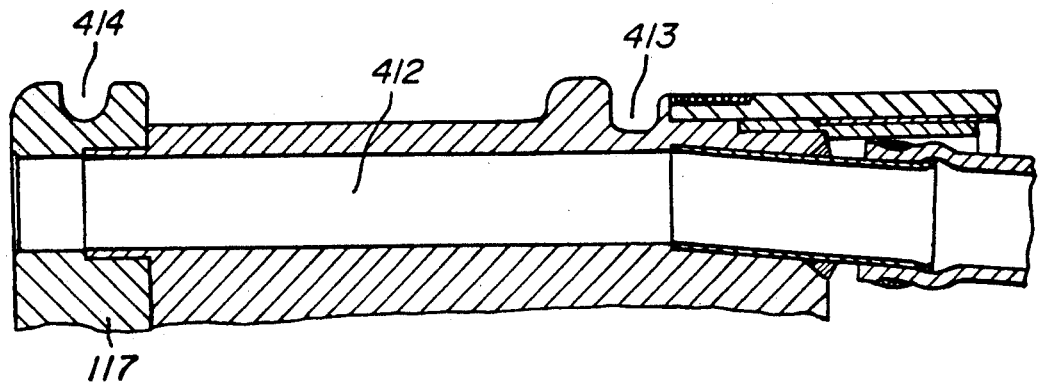
Figure 21G:
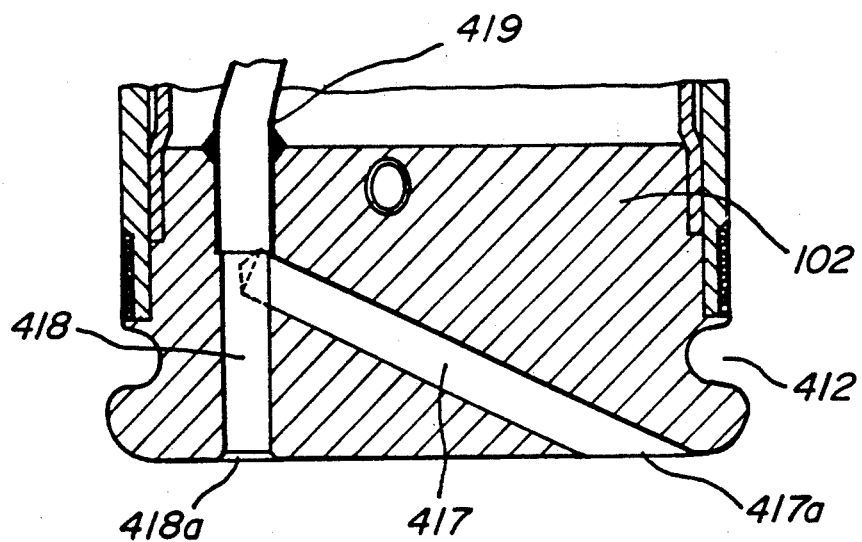

FIG. 19 is a longitudinal cross section showing an eleventh embodiment of the ultrasonic endoscope according to the invention. FIG. 20 is a front view of the endoscope, and FIGS. 21a to 21g are cross sectional views cut along lines A—A to G—G. Also in the present embodiment, portions similar to those illustrated in the previous embodiments are denoted by the same reference numerals used in the previous embodiments. In the present embodiment, the rotor 101 mounting the ultrasonic vibrating unit 112 is rotatably secured to the distal end support member 102 by means of ball bearings 103, 104, spacer 105 and a sleeve-like member 401. The ultrasonic vibrating unit 112 is surrounded by the distal end cap 106 having the ultrasonic wave transmitting window 107 thin the cap 106 is filled with the ultrasonic wave, transmitting medium 108 and the tip opening of cap 106 is closed in a liquid tight manner with the aid of the O-ring 110 and the screw 111. The rotor 101 is coupled with the motor provided in the ultrasonic operating member 14 (see FIG. 1) via the flexible hollow shaft 113 which is covered by a flexible tube 113a. A part of the front end of the distal end support member 102 is projected in the direction parallel to the longitudinal axis of the probe distal end to form a projection 102d and the cylindrical member 100 is secured to the front end of this projection 102d, and the optical viewing including the objective lens 122 and the image guide fiber 123, the optical illumination system having the illumination lens 125 and the light guide fibers 126, and liquid and air supply conduit 127 with the nozzle 127b are provided in the cylindrical member 100. The front end of distal end cap 107 and the cylindrical member 100 are secured to the distal end cover 117. A spacer formed between the distal end cap 107, the projection 102d of distal end support member 102, the cylindrical member 100 and the distal end cover 117 is filled with the filling agent 410, and the sheet 411 made of ultrasonic wave absorbing material such as urethane rubber and silicon rubber is applied on the inner wall of the projection 102d of distal end support member, so that the scattering of ultrasonic wave can be prevented. Within the projection 102d of distal end support member 102 is formed a suction conduit 412 which is exposed to the front end through the distal end cover 117. In the outer surfaces of the distal end support member 102 and distal end cover 117 there are formed recesses 413 and 414 into which both side edges of a balloon are to be clamped. In the front end surface of the support member 102 there is exposed an opening 415 of the liquid supply conduit for supplying the liquid into the balloon. Further openings 417a, 418a of conduits 417, 418 for sucking the liquid from the balloon are formed in the end surface of the distal end support member 102. It should be noted that the one of the conduits 417 is inclined within the support 102 and is communicated with the other conduit 418 as illustrated in FIG. 21g, so that only a single tube 419 communicated with the conduits is extended from the support 102 toward the proximal end. The image guide fiber 123 and light guide fibers 127 are covered by flexible protection tubes, respectively, and these fibers with the protection tubes are further covered by a single flexible protection tube 420. A flexible tube 421 connected to the conduit 127 is also inserted into the tube 420.

In case of effecting the diagnosis with the aid of the ultrasonic endoscope of the present embodiment, the probe is inserted into a cavity of a patient, while the inside of the cavity, is observed forwardly. After the distal end of the probe is positioned at a desired point, the ultrasonic vibrating unit 112 is rotated to display the ultrasonic image on the monitor screen, and the deaerated liquid is supplied into the balloon to inflate the balloon such that the balloon is urged against the cavity wall. After the diagnosis is finished the deaerated liquid is discharged from the balloon via the conduit openings 417a, 418a, and after it has been confirmed from the ultrasonic image on the monitor that the balloon is shrunk sufficiently, the rotation of the ultrasonic vibrating unit is stopped, and then the probe is removed from the patient.

In the above explained embodiment, since there are provided two openings 417a, 418a for sucking the liquid out of the balloon on both sides of the assembly of the distal end cap 107 and projection 102d, the balloon is hardly sucked onto the openings and further even though one of the openings is clogged by the balloon, the liquid can be effectively discharged from the balloon and is hardly remained in the balloon. Moreover, the distal end cap 107, ultrasonic vibrating unit 112, flexible shaft 113 and flexible tube 113a are secured to the sleeve 401 to form an integral assembly, and the assembly can be easily removed from the endoscope. Therefore the flexible tube 113a or the ultrasonic vibrating unit 112 can be easily exchanged.

Although the embodiments of the present invention have been described herein with reference to the accompanying drawings, obviously many modifications and changes may be made of those skilled in this art without departing from the scope of the invention.

What is claimed is:

1. An ultrasonic endoscope apparatus for viewing a body cavity, said ultrasonic endoscope apparatus comprising:

an insertion section adapted to be inserted into the body cavity to be observed and having a proximal end and a distal end;

a first distal end support member having a front end and a rear end, said rear end being secured to the distal end of the insertion section;

an ultrasonic wave transmission window having a rear end and a front end, said rear end of the ultrasonic wave transmission window being secured to said front end of the first distal end support member and said ultrasonic wave transmission window extending around an axis of the first distal end support member to form a space therein;

an ultrasonic vibrating unit provided in said space to transmit and receive an ultrasonic wave through said ultrasonic wave transmission window;

a second distal end support member having a front end and a rear end, said rear end of said second distal end support member being secured to the front end of the first distal end support member and said second distal end support member being arranged near said ultrasonic transmission window in parallel with the ultrasonic wave transmission window; and an optical viewing means arranged substantially within said second distal end support member for providing both a forward observing field and an oblique observing field;

wherein said ultrasonic vibrating unit is an electronic scan type ultrasonic vibrating unit emitting an ultrasonic beam over substantially a full scope of the compass.

2. An ultrasonic endoscope apparatus for viewing a body cavity, said ultrasonic endoscope apparatus comprising:

an insertion section adapted to be inserted into the body cavity to be observed and having a proximal end and a distal end;

a first distal end support member having a front end and a rear end, said rear end being secured to the distal end of the insertion section;

an ultrasonic wave transmission window having a rear end and a front end, said rear end of the ultrasonic wave transmission window being secured to said front end of the first distal end support member and said ultrasonic wave transmission window extending around an axis of the first distal end support member to form a space therein;

an ultrasonic vibrating unit provided in said space to transmit and receive an ultrasonic wave through said ultrasonic wave transmission window;

a second distal end support member having a front end and a rear end, said rear end of said second distal end support member being secured to the front end of the first distal end support member and said second distal end support member being arranged near said ultrasonic transmission window in parallel with the ultrasonic wave transmission window;

an optical viewing means arranged substantially within said second distal end support member for providing one of a forward observing field and an oblique observing field; and a distal end cap secured to the front end of said ultrasonic transmission window and the front end of said second distal end support member.

3. An ultrasonic endoscope apparatus according to claim 2, further comprising a pipe means for supplying a liquid, said pipe means being located adjacent to said ultrasonic transmission window, at least a portion of said pipe means through which an ultrasonic beam is transmitted being made of a material having an ultrasonic transmission property.

4. An ultrasonic endoscope apparatus according to claim 2, further comprising a connecting cover having a truncated cone shape, said first distal end support member having a larger diameter than said distal end cap, said first distal end support member and said distal end cap being connected by said connecting cover so that a portion between said first distal end cap and said distal end support member is covered by said connecting cover.

5. An ultrasonic endoscope apparatus according to claim 2, further comprising a cylindrical connecting cover having an inner cover and an outer cover, said inner cover being made of a hard plastic and provided with a passage for transmitting an ultrasonic beam, said outer cover being made of a material having an ultrasonic transmission property.

6. An ultrasonic endoscope apparatus according to claim 2, wherein said first distal end support member is provided with a motor for rotating said ultrasonic vibrating unit.

7. An ultrasonic endoscope apparatus according to claim 2, further comprising an optical illumination system and an air and liquid supply pipe, said optical viewing means, said optical illumination system and said pipe being provided in parallel with said distal end cap, portions of said optical viewing means and said optical illumination system to which an ultrasonic beam is projected being made of a plastic material, and a portion of said pipe being made of an elastomeric rubber material.

8. An ultrasonic endoscope according to claim 2, wherein said optical viewing means comprises an imaging system and an illumination system, and said second distal end support member comprises first and second flexible protection tubes respectively having said imaging system and said illumination system disposed therein, and a third flexible protection tube having said first and second flexible tubes disposed therein.

9. An ultrasonic endoscope according to claim 2, further comprising a flexible hollow shaft connected to the ultrasonic vibrating unit and a flexible tube accommodating said flexible shaft, wherein said ultrasonic vibrating unit, said distal end cap, said flexible hollow shaft and said flexible tube are formed into a single body which is detachably mounted on the first distal end support member.

10. An ultrasonic endoscope apparatus according to claim 2, wherein said second distal end support member is formed as a cylindrical member and a front end of the cylindrical member is provided in an opening formed in said distal end cap.

11. An ultrasonic endoscope apparatus according to claim 10, further comprising an acoustic absorption member provided at least an outer peripheral portion of said cylindrical member to which an ultrasonic beam is projected.

12. An ultrasonic endoscope apparatus according to claim 10, further comprising an end cover covering an end portion of said cylindrical member and an end portion of said distal end cap.

13. An ultrasonic endoscope apparatus according to claim 12, further comprising a first balloon provided on an outer periphery of said end cap, and a second balloon provided on an outer periphery of said first distal end support member, and said first distal end support member includes a conduit for supplying a liquid.

14. An ultrasonic endoscope apparatus according to claim 12, further comprising a balloon having a peripheral portion of one end thereof connected to said end cap, and a peripheral portion of the other end thereof connected to said first distal end support member, and said first distal end support member includes a liquid supply conduit and a liquid suction conduit.

15. An ultrasonic endoscope according to claim 14, further comprises an ultrasonic wave absorbing member arranged between the distal end cap and the cylindrical member, and a pair of openings of the liquid suction conduit are exposed in the end surface of the first distal end support member on respective sides of the distal end 16. An ultrasonic endoscope apparatus according to claim 10, wherein said distal end cap is provided with a cylindrical cover extending to and connected to said first distal end support member and said second distal end support member.

17. An ultrasonic endoscope apparatus according to claim 16, wherein said distal end cap provided with said cylindrical cover is made of a material having an ultrasonic transmission property.

18. An ultrasonic endoscope apparatus according to claim 10, further comprising an acoustic absorption member provided between said distal end cap and said cylindrical member.

19. An ultrasonic endoscope apparatus according to claim 2, wherein said optical viewing means is arranged within said second distal end support member such that an optical axis of the optical viewing means extends substantially in parallel with the axis of the ultrasonic wave transmission window to obtain the forward observing field.

20. An ultrasonic endoscope apparatus according to claim 2, wherein said ultrasonic wave transmission window and said distal end cap are formed as a single integral body.

21. An ultrasonic endoscope apparatus according to claim 2, wherein said ultrasonic vibrating unit comprises an ultrasonic vibrating element and a bearing member for supporting the ultrasonic vibrating element rotatably about an axis which is disposed in parallel with the axis of the first distal end support member.

22. An ultrasonic endoscope apparatus according to claim 2, wherein said ultrasonic wave transmission window extends around said axis of the first distal end support member through an angle of at least approximately 300°.

* * * * *